United States Patent
Norman et al.

(10) Patent No.: US 8,129,505 B2
(45) Date of Patent: Mar. 6, 2012

(54) COMB POLYMERS

(75) Inventors: Timothy John Norman, Slough (GB); Benjamin Charles De Candole, Slough (GB); Mezher Hussein Ali, Slough (GB)

(73) Assignee: UCB Pharma S.A., Brussels (BE)

( * ) Notice: Subject to any disclaimer, the term of this patent is extended or adjusted under 35 U.S.C. 154(b) by 699 days.

(21) Appl. No.: 12/066,966

(22) PCT Filed: Sep. 12, 2006

(86) PCT No.: PCT/GB2006/003376
§ 371 (c)(1),
(2), (4) Date: Mar. 14, 2008

(87) PCT Pub. No.: WO2007/031734
PCT Pub. Date: Mar. 22, 2007

(65) Prior Publication Data
US 2008/0220005 A1 Sep. 11, 2008

(30) Foreign Application Priority Data
Sep. 14, 2005 (GB) .................................. 0518771.1
Jan. 9, 2006 (GB) .................................. 0600315.6

(51) Int. Cl.
*C07K 17/06* (2006.01)
*C07K 1/04* (2006.01)
*C07K 16/00* (2006.01)
*C07K 1/13* (2006.01)
*G01N 33/544* (2006.01)

(52) U.S. Cl. .................. 530/391.7; 530/402; 530/387.1; 436/528; 436/544

(58) Field of Classification Search .......................... None
See application file for complete search history.

(56) References Cited

U.S. PATENT DOCUMENTS

| | | | |
|---|---|---|---|
| 4,741,900 A | 5/1988 | Alvarez et al. |
| 4,946,778 A | 8/1990 | Ladner et al. |
| 5,219,996 A | 6/1993 | Bodmer et al. |
| 5,223,409 A | 6/1993 | Ladner et al. |
| 5,262,524 A | 11/1993 | Anderson et al. |
| 5,403,484 A | 4/1995 | Ladner et al. |
| 5,427,908 A | 6/1995 | Dower et al. |
| 5,516,637 A | 5/1996 | Huang et al. |
| 5,571,698 A | 11/1996 | Ladner et al. |
| 5,580,717 A | 12/1996 | Dower et al. |
| 5,585,089 A | 12/1996 | Queen et al. |
| 5,658,727 A | 8/1997 | Barbas et al. |
| 5,677,425 A | 10/1997 | Bodmer et al. |
| 5,698,426 A | 12/1997 | Huse |
| 5,733,743 A | 3/1998 | Johnson et al. |
| 5,750,753 A | 5/1998 | Kimae et al. |
| 5,780,225 A | 7/1998 | Wigler et al. |
| 5,821,047 A | 10/1998 | Garrard et al. |
| 5,969,108 A | 10/1999 | McCafferty et al. |
| 6,214,345 B1 | 4/2001 | Firestone et al. |

FOREIGN PATENT DOCUMENTS

| | | |
|---|---|---|
| EP | 0948544 A1 | 2/2003 |
| WO | 92/02551 A1 | 2/1992 |
| WO | 92/18619 A1 | 10/1992 |
| WO | 92/22583 A2 | 12/1992 |
| WO | 93/11236 A1 | 6/1993 |
| WO | 95/15982 A2 | 6/1995 |
| WO | 95/20401 A1 | 8/1995 |
| WO | 96/30421 A1 | 10/1996 |
| WO | 97/18247 A1 | 5/1997 |
| WO | 97/47661 A1 | 12/1997 |
| WO | 98/25971 A1 | 6/1998 |
| WO | 99/15549 A2 | 4/1999 |
| WO | 99/28362 A1 | 6/1999 |
| WO | 03/097635 A1 | 11/2003 |
| WO | 2004/051268 A1 | 6/2004 |
| WO | 2004/106377 A1 | 12/2004 |
| WO | 2004/113394 A2 | 12/2004 |

(Continued)

OTHER PUBLICATIONS

Malz et al. Synthesis of functional polymers by atom transfer radical polymerization. Macromol. Chem. Phys. 1999, vol. 200, Issue 3, pp. 642-651.*

Malz, H. et al., Synthesis of Functional Polymers by Atom Transfer Radical Polymerization, Macromolecular Chemistry and Physics, Mar. 1999, pp. 642-651, vol. 200.

Kohler et al., "Continuous cultures of fused cells secreting antibody of predefined specificity", Nature, vol. 256, 1975, 495-497.

Kozbor et al., "The production of monoclonal antibodies from human lymphocytes", Immunology Today, 4(3), 1983, 72-79.

Cole et al., "The EBV-Hybridoma technique and its application to human lung cancer", Monoclonal Antibodies and Cancer Therapy, 1985, 77-96.

(Continued)

*Primary Examiner* — Shafiqul Haq
(74) *Attorney, Agent, or Firm* — McDonnell Boehnen Hulbert & Berghoff LLP

(57) ABSTRACT

The present invention provides a process for producing a comb polymer comprising the steps of: a) providing: (i) (w+z) molar equivalents of a monomer; (ii) one molar equivalent of an initiator compound of formula (IX), wherein $B^3$ represents a halogen, $B^2$ represents H or a halogen, $Y^1$ represents a group capable of attaching the residue of an antibody or fragment thereof or capable of being converted into such a group, L represents a linker group, y is 1, 2 or 3, w is at least 1 and z is 0 or greater; (iii) a catalyst capable of catalysing the polymerization of a plurality of the monomers to produce the comb polymer; and b) causing the catalyst to catalyse, in combination with the initiator, the polymerization of a plurality of the monomers (i) to produce the comb polymer.

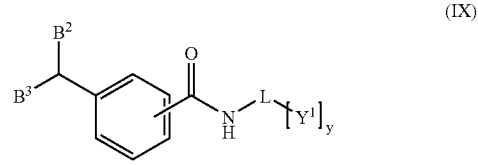

(IX)

10 Claims, No Drawings

FOREIGN PATENT DOCUMENTS

| | | |
|---|---|---|
| WO | WO2004/113394 | 12/2004 |
| WO | 2005/003169 A2 | 1/2005 |
| WO | 2005/003170 A2 | 1/2005 |
| WO | 2005/003171 A2 | 1/2005 |
| WO | 2005/061005 A2 | 7/2005 |
| WO | 2005/113605 A1 | 12/2005 |

OTHER PUBLICATIONS

Brinkman et al., "Phage display of disulfide-stabilized Fv fragments", Journal of Immunological Methods, vol. 182, 1995, 41-50.

Ames et al., "Conversion of murine Fabs isolated from a combinatorial phage display library to full length immunoglobulins", Journal of Immunological Methods, vol. 184, 1995, 177-186.

Kettleborough et al., "Isolation of tumor cell-specific single-chain Fv from immunized mice using phage-antibody libraries and the reconstruction of whole antibodies from these antibody fragments", Eur. J. Immunol., vol. 24, 1994, 952-958.

Persic et al., "An integrated vector system for the eukaryotic expression of antibodies or their fragments after selection from phage display libraries", Gene, vol. 187, 1997, 9-18.

Burton et al., "Human antibodies from combinatorial libraries", Advances in Immunology, vol. 57, 1994, 191-280.

Suckling, C. J., "Minor groove binders 1998-2004", Expert Opin. Ther. Patents, 14(12), 2004, 1693-1724.

Field, L. et al., "Organic disulfides and related substances. IV. Thiolsulfonates and disulfides containing 2-Aminoethyl Moieties", Department of Chemistry, Vanderbilt University, Nashville, Tennessee, JACS, vol. 83, 1961, 4414-17.

Dubowchik, G. M. et al., "Cathepsin B-labile dipeptide linkers for lysosomal releaseof doxorubicin from internalizing immunoconjugates: Model studies of enzymatic drug release and antigen-specific in vitro anticancer activity" Bioconjugate Chem., vol. 13, 2002, 855-869.

Linn, C. P. et al "Synthesis of serine-AMC-carbamate: A fluorogenic tryptophanase substrate", Analytical Biochemistry, vol. 200, 1992, 400-404.

Malz et al, "Synthesis of functional polymers by atom transfer radical polymerization", Macromolecular Chemistry and Physics, 200(3), 1999, 642-651.

\* cited by examiner

COMB POLYMERS

This application is a National Stage filing under 35 U.S.C. 371 of International Application No. PCT/GB2006/003376, filed Sep. 12, 2006, which claims priority to Great Britain patent applications nos. 0518771.1, filed Sep. 14, 2005, and 0600315.5, filed Jan. 9, 2006.

The present invention relates to compounds for use in attaching effector molecules to antibodies. More specifically the invention relates to molecules comprising antibody-comb polymer conjugates to which effector molecules and solubilising moieties are attached. Methods for the production of such molecules, and pharmaceutical compositions containing them, are also provided.

The binding specificity of antibodies can be used to deliver effector molecules, such as drugs, to specific therapeutic targets such as tumor cells. Effector molecules may be attached to antibodies using various methods including for example, direct attachment (see for example, U.S. Pat. No. 5,677,425; EP0948544) or attachment via a linker (see for example U.S. Pat. No. 6,214,345).

Polyethylene glycol (PEG) may be attached to proteins or polypeptides to reduce immunogenicity, increase circulating half-life in vivo and to increase the solubility of the protein. PEG may be attached to the protein as a comb polymer (see for example WO2004/113394).

The present invention provides new antibody-comb polymer conjugates to which both effector molecules and solubilising moieties may be attached.

The present invention therefore provides compounds consisting essentially of one or more antibodies linked to one or more comb polymers in which the comb polymer comprises one or more effector molecules and optionally one or more solubilising groups.

Accordingly the present invention provides a compound of formula (Ia) or (Ib):

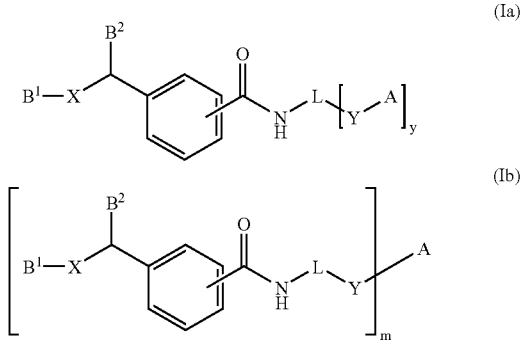

wherein:
y is 1, 2 or 3
m is 1, 2, 3, 4, 5, 6, 7, 8, 9 or 10
$B^1$ represents a halogen
$B^2$ represents H or a halogen
A represents the residue of an antibody or fragment thereof
Y represents a spacer group
L represents a linker group
X represents a comb polymer moiety comprising w equivalents of one or more effector molecules and z equivalents of one or more water solubilising moieties, wherein w is at least 1, and z is 0 or greater.

Preferably the compound of formula (Ia) has the formula (IIa).

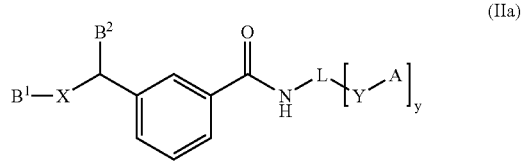

Preferably the compound of formula (Ib) has the formula (IIb).

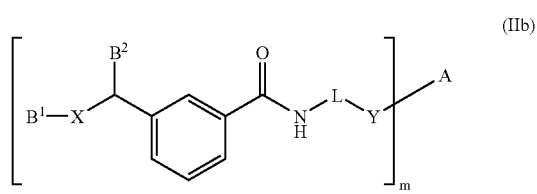

Suitably m is 1 or 2.

In one embodiment, y is 1.

Preferably the halogen for use in the present invention is either bromine or chlorine. Preferably chlorine.

As used herein, the term "residue" will be understood to mean that portion of an antibody or fragment thereof which remains after it has undergone a substitution reaction as such terminology is familiar to the person skilled in the art.

The residue A includes residues of whole antibodies and functionally active fragments or derivatives thereof and may be, but are not limited to, polyclonal, monoclonal, humanized or chimeric antibodies, single chain antibodies, Fab fragments, Fab' and F(ab')$_2$ fragments and epitope-binding fragments of any of the above.

It will be appreciated that the residue A includes residues of cross-linked antibodies. Such cross-linked antibodies are well known in the art (see for example U.S. Pat. No. 5,262,524). The term 'cross-linked antibodies' as used herein refers to two, three or four antibodies or fragments thereof, linked by a connecting structure. The connecting structure may be any molecular structure capable of linking the antibodies or fragments thereof together see for example WO92/22583 which describes tri- and tetra-valent monospecific antigen-binding proteins comprising Fab' fragments bound to each other by a connecting structure. In one embodiment the cross-linked antibody comprises three antibody fragments, preferably Fab' fragments connected as described in WO2005113605, published 1 Dec. 2005. In another embodiment the cross-linked antibody comprises two antibody fragments connected as described in WO2005/061005.

Antibodies include immunoglobulin molecules and immunologically active portions of immunoglobulin molecules, i.e. molecules that contain an antigen binding site that specifically binds an antigen. The immunoglobulin molecules of the invention can be of any class (e.g. IgG, IgE, IgM, IgD or IgA) or subclass of immunoglobulin molecule.

Monoclonal antibodies may be prepared by any method known in the art such as the hybridoma technique (Kohler & Milstein, *Nature*, 1975, 256, 495-497), the trioma technique, the human B-cell hybridoma technique (Kozbor et al., *Immunology Today*, 1983, 4, 72) and the EBV-hybridoma technique (Cole et al., "Monoclonal Antibodies and Cancer Therapy", pp. 77-96, Alan R. Liss, Inc., 1985).

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., *Proc. Natl. Acad. Sci. USA*, 1996, 93(15), 7843-7848, WO 92/02551, WO2004/051268 and WO2004/106377.

Humanized antibodies are antibody molecules comprising one or more complementarity determining regions (CDRs) from a non-human species and a framework region from a human immunoglobulin molecule (see, for example, U.S. Pat. No. 5,585,089).

Chimeric antibodies are those antibodies encoded by immunoglobulin genes that have been genetically engineered so that the light and heavy chain genes are composed of immunoglobulin gene segments belonging to different species.

The antibodies for use in the present invention can also be generated using various phage display methods known in the art and include those disclosed by Brinkman et al., *J. Immunol. Methods*, 1995, 182, 41-50; Ames et al., *J. Immunol. Methods*, 1995, 184, 177-186; Kettleborough et al. *Eur. J. Immunol.*, 1994, 24, 952-958; Persic et al., *Gene*, 1997 187, 9-18; and Burton et al., *Advances in Immunology*, 1994, 57, 191-280; WO 90/02809; WO 91/10737; WO 92/01047; WO 92/18619; WO 93/11236; WO 95/15982; and WO 95/20401; and U.S. Pat. Nos. 5,698,426; 5,223,409; 5,403,484; 5,580, 717; 5,427,908; 5,750,753; 5,821,047; 5,571,698; 5,427,908; 5,516,637; 5,780,225; 5,658,727; 5,733,743; and 5,969,108. Techniques for the production of single chain antibodies, such as those described in U.S. Pat. No. 4,946,778, can also be adapted to produce single chain antibodies. Also, transgenic mice, or other organisms, including other mammals, may be used to express humanized antibodies.

In one example the antibody fragments are Fab' fragments which possess a native or a modified hinge region. A number of modified hinge regions have already been described, for example, in U.S. Pat. No. 5,677,425, WO9915549, and WO9825971 and these are incorporated herein by reference Other antibody fragments include those described in WO2005003169, WO2005003170 and WO2005003171.

Suitably the antibody fragments for use in the present invention contain a single free thiol, preferably in the hinge region.

The antibodies or fragments thereof of the present invention will in general be capable of selectively binding to an antigen. The antigen may be any cell-associated antigen, for example a cell surface antigen on cells such as bacterial cells, yeast cells, T-cells, endothelial cells or tumour cells, or it may be a soluble antigen. Antigens may also be any medically relevant antigen such as those antigens upregulated during disease or infection, for example receptors and/or their corresponding ligands. Particular examples of cell surface antigens include adhesion molecules, for example integrins such as β1 integrins e.g. VLA-4, E-selectin, P selectin or L-selectin, CD2, CD3, CD4, CD5, CD7, CD8, CD11a, CD11b, CD18, CD19, CD20, CD23, CD25, CD33, CD38, CD40, CD45, CDW52, CD69, CD70, CD134, carcinoembryonic antigen (CEA), MUC-1, MHC Class I and MHC Class II antigens, and VEGF, and where appropriate, receptors thereof. Soluble antigens include interleukins such as IL-1, IL-2, IL-3, IL-4, IL-5, IL-6, IL-8, IL-12, IL-16 or IL-17, viral antigens for example respiratory syncytial virus or cytomegalovirus antigens, immunoglobulins, such as IgE, interferons such as interferon α, interferon β or interferon γ, tumour necrosis factor-α, tumor necrosis factor-β, colony stimulating factors such as G-CSF or GM-CSF, and platelet derived growth factors such as PDGF-α, and PDGF-β and where appropriate receptors thereof.

The spacer group for use in the present invention, will suitably comprise any moiety familiar to the person skilled in the art which is capable of forming a bridge between the linker and the antibody or fragment thereof. In particular the spacer group Y will suitably comprise any moiety familiar to the person skilled in the art which is capable of forming a bridge between the linker L and the residue A. In one example, where A is the residue of an antibody or a fragment thereof containing a cysteine residue the corresponding spacer group Y will suitably be succinimide (i.e. the reaction product of a maleimide residue with the cysteine-containing polypeptide residue A via a thiol linkage and the linker L through the maleimide nitrogen atom).

The linker group L will suitably comprise any moiety familiar to the person skilled in the art which is capable of forming a bridge between the spacer group Y and the N atom of the amide group. L may be straight chain or branched.

Typical examples of L include:

—$(CH_2)_n$— wherein n is 1, 2, 3, 4, 5 or 6;

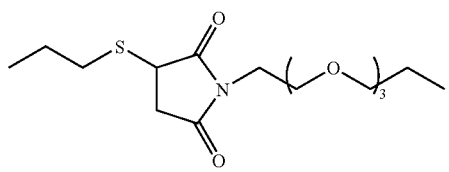

Hence in one embodiment, L represents —$(CH_2)_n$—. Preferably n is 2.

In another embodiment, L represents

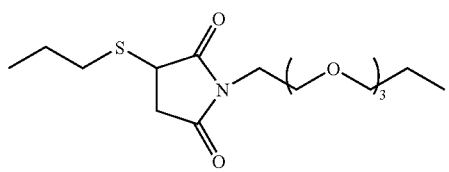

In the present invention, X represents a comb polymer moiety comprising w equivalents of one or more effector molecules and z equivalents of a water solubilising moiety.

X therefore suitably comprises the components of formula III and IV in any order.

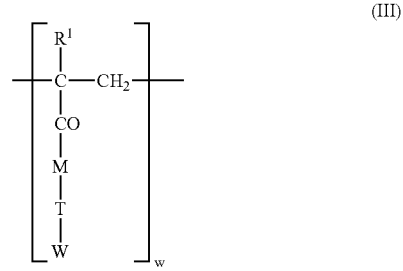

(III)

-continued

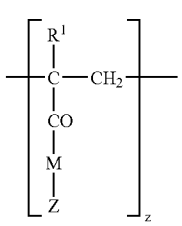

(IV)

wherein:
w is at least 1.
z is 0 or greater.
T is absent or a linker group
W is an effector molecule
Z is a water solubilising moiety
M is NH or O
$R^1$ is methyl or H
Suitably M is NH.

Typically w is between 1 and 300. Suitably w is between 1 and 200. In one embodiment w is between 1 and 100. In one embodiment w is between 1 and 50. In one embodiment w is between 1 and 20.

Typically z is between 0 and 300. Suitably z is between 0 and 200. Suitably z is at least 1. In one embodiment z is between 1 and 200. In one embodiment z is between 1 and 100. In one embodiment z is between 1 and 50. In one embodiment z is between 1 and 20.

The total amount of compounds III and IV (i.e. w+z) present in X is at least 1. Typically w+z is between 1 and 300. In one embodiment w+z is 15. In one embodiment w+z is 13. In one embodiment w+z is 41. In one embodiment w+z is 96. In one embodiment w+z is 165. In one embodiment w+z is 262.

Where w+z is 41 preferably w is 6 and preferably z is 35.

Suitable linkers, T, where present, are well known in the art. Particularly preferred linkers are self-immolative linkers. Examples of self-immolative linkers are described in U.S. Pat. No. 6,214,345. Particularly preferred is a linker having the formula (V) below:

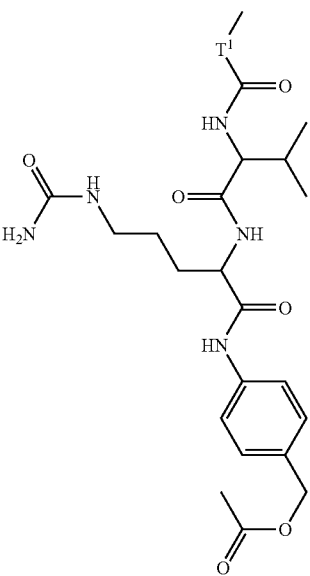

(V)

wherein $T^1$ represents $[CH_2]_t$ or $CH_2CH_2[OCH_2CH_2]_n$ where t is between 1 and 10 and n is between 5 and 100. In one embodiment, $T^1$ represents $[CH_2]_t$. In one embodiment t is 5. In one embodiment $T^1$ represents $CH_2CH_2[OCH_2CH_2]_n$. In one embodiment n is between 5 and 30, preferably either 12 or 24. In another embodiment n is between 40 and 100, preferably between 40 and 80.

It will be appreciated that the effector molecule, W, may comprise a single effector molecule or two or more such molecules so linked as to form a single moiety. Examples of such moieties include effector molecules linked by branched connecting structures.

It will also be appreciated that where w is greater than 1, each W can be the same or different.

Effector molecules for use in the present invention include biologically active compounds suitable for medicinal or diagnostic use in the treatment of animals, including humans. Such molecules include nucleic acids (e.g. DNA and RNA), carbohydrates, lipids, proteins, polypeptides, peptides, peptidomimetics, small molecules and other drugs such as those listed in U.S. Pat. No. 6,214,345, column 8, line 49 to column 9 line 13.

Examples of effector molecules may include cytotoxins or cytotoxic agents including any agent that is detrimental to (e.g. kills) cells. Examples include minor-groove binders (see for example the compounds provided in Expert Opinion in Therapeutic Patents, 2004, 14, 1693-1724), combrestatins, dolastatins, auristatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In one embodiment the cytotoxic agent is the residue of a 3-substituted 1-(chloromethyl)-1,2-dihydro-3H-[ring fused indol-5-yl(amine-derived)] compound or analogue thereof as described in WO03097635. In one embodiment the cytotoxic agent is the residue of 1-(chloromethyl)-3-[(2E)-3-(4-methoxyphenyl)-2-propenoyl]-1,2-dihydro-3H-benzo[e]indol-5-amine.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa, chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}In$ and $^{90}Y$, $Lu^{177}$, $Bismuth^{213}$, $Californium^{252}$, $Iridium^{192}$ and $Tungsten^{188}$/$Rhenium^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and acquorin; and suitable radioactive nuclides include $^{125}I$, $^{131}I$, $^{111}In$ and $^{99}Tc$.

Other effector molecules may include proteins or polymers or other compounds that may be used to extend the half-life and/or decrease the immunogenicity of the compound of the present invention. Examples of suitable proteins include albumin and albumin binding proteins or albumin binding fatty acids. Examples of suitable polymers include those described below, in particular optionally substituted straight or branched chain polyalkylene, polyalkenylene, or polyoxyalkylene polymers such as poly(ethylene glycol).

The water solubilising moiety, Z, for use in the present invention includes any suitable solubilising moiety known in the art such as charged species (positive and negative) such as acids, amines, quaternary amines, zwitterionic species such as amino acids, polymers such as polyethylene glycol, mono or poly hydroxyalkanes, alcohols (mono, di and tri) and sugars. A particular example of a suitable amine is phosphocholine.

Examples of suitable polymers include any synthetic or naturally occurring substantially water-soluble, substantially non-antigenic polymer including, for example, optionally substituted straight or branched chain polyalkylene, polyalkenylene, or polyoxyalkylene polymers or branched or unbranched polysaccharides, e.g. a homo- or hetero-polysaccharide such as lactose, amylose, dextran or glycogen. Particular optional substituents which may be present on the above-mentioned synthetic polymers include one or more hydroxy, methyl or methoxy groups. Particular examples of synthetic polymers include optionally substituted straight or branched chain poly(ethyleneglycol), poly(propyleneglycol), poly(vinylalcohol) or derivatives thereof, especially optionally substituted poly(ethyleneglycol) such as methoxypoly(ethyleneglycol).

Preferably the polymer is a polyalkylene oxide such as polyethylene glycol (PEG). As regards attaching PEG moieties in general, reference is made to "Poly(ethyleneglycol) Chemistry, Biotechnical and Biomedical Applications", 1992, J. Milton Harris (ed), Plenum Press, New York; "Poly(ethyleneglycol) Chemistry and Biological Applications", 1997, J. Milton Harris and S. Zalipsky (eds), American Chemical Society, Washington D.C.; and "Bioconjugation Protein Coupling Techniques for the Biomedical Sciences", 1998, M. Aslam and A. Dent, Grove Publishers, New York.

The size of the polymer may be varied as desired, but will generally be in an average molecular weight range from 150 to 100,000 Da, preferably from 2,000 to 50,000 Da, more preferably from 10,000 to 40,000 Da and still more preferably from 20,000 to 40,000 Da.

It will be appreciated that where z is greater than 1, each Z can be the same or different.

In one embodiment the water solubilising moiety Z is:

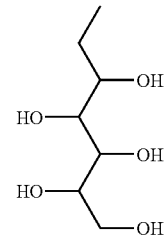

In one embodiment the water solubilising moiety Z is:

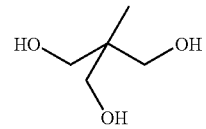

In one embodiment the water solubilising moiety Z is:

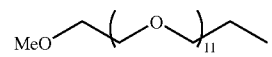

In one embodiment the water solubilising moiety Z is:

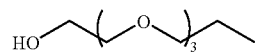

In one embodiment the water solubilising moiety Z is:

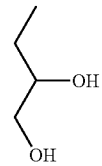

Also provided by the present invention are valuable intermediate compounds suitable for the attachment of an antibody. Said compounds consist essentially of the following elements: a comb polymer comprising one or more effector molecules and optionally one or more solubilising groups and a group capable of attaching the residue A or capable of being converted into such a group.

Accordingly the present invention provides compounds according to formula (VI)

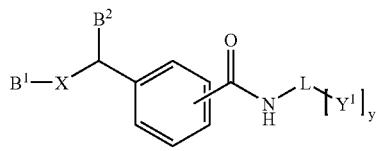
(VI)

wherein:
$Y^1$ represents a group capable of attaching the residue A, or capable of being converted into such a group
L, X, $B^1$, $B^2$ and y are as described herein above.
$Y^1$ is a group known in the art suitable for linking L and A or capable of being converted into such a group. For example $Y^1$ may be a protected derivative i.e. is masked by another group, a 'protecting group' to prevent $Y^1$ from reacting with other groups in the compound. Such protected derivatives are capable of being readily converted to a group capable of attaching A. Examples of such groups are protected thiols where the protecting group can be readily removed to provide a free thiol for reaction with the residue A. Conditions for removal of the protecting group are preferably such that the biological activity of the components of the comb polymer are not affected. Suitable protected thiols are known in the art and include thioethers (e.g. trityl protected), thioesters (e.g. acetyl or propionyl protected), thiocarbonates, thiocarbamates and sulfenyls.

The group $Y^1$ may be attached to the residue A through any available amino acid side-chain or terminal amino acid functional group located in the antibody or fragment thereof, for example any free amino, imino, thiol, hydroxy or carboxyl group. Such amino acids may occur naturally in, for example, the antibody fragment or may be engineered into the antibody or fragment thereof using recombinant DNA methods (see, for example, U.S. Pat. No. 5,219,996 and U.S. Pat. No. 5,677,425). In a preferred aspect of the invention the two groups are covalently linked through a thiol group of a cysteine residue located in the antibody or fragment thereof, preferably in the hinge. The covalent linkage will generally be a disulphide bond or a sulphur-carbon bond, preferably the latter. In one example where a thiol group is used as the point of attachment appropriately activated groups, for example thiol-selective derivatives such as maleimide may be used.

$Y^1$ may be any suitable group including any of those listed in WO2004/113394 pages 9-11.

$Y^1$ may be —S—S—$R^2$ wherein $R^2$ is any straight or branched chain $C_{1-6}$ alkyl or substituted aromatic.

$Y^1$ may be

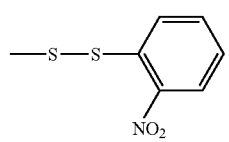

$Y^1$ may be

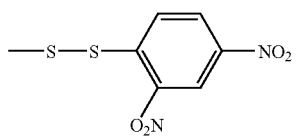

$Y^1$ may be

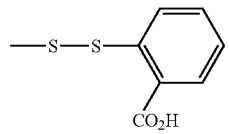

$Y^1$ may be

$Y^1$ may be

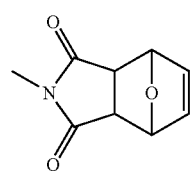

$Y^1$ may be

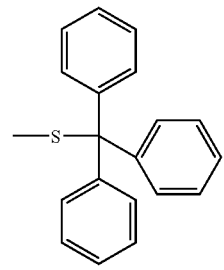

$Y^1$ may be
—SH
$Y^1$ may be
—S—$SO_3^-$

As used herein, the term "$C_{1-6}$ alkyl" refers to straight-chained and branched alkyl groups containing 1 to 6 carbon atoms. Such groups are methyl, ethyl, propyl, butyl, pentyl and hexyl. Preferably $R^2$ is selected from methyl, ethyl, n-propyl, isopropyl, n-butyl, isobutyl, sec-butyl and tert-butyl. Preferably $R^2$ is tert-butyl.

In a preferred feature, $Y^1$ represents

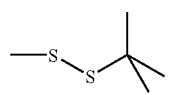

Accordingly, one illustrative compound of formula (VI) above is represented by the compound of formula (VII):

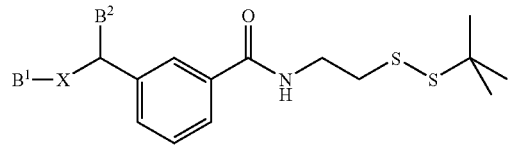

(VII)

In a preferred feature, $Y^1$ represents a maleimide derivative attached to the remainder of the molecule through the maleimide nitrogen atom. Accordingly, one illustrative compound of formula (VI) above is represented by the compound of formula (VIII):

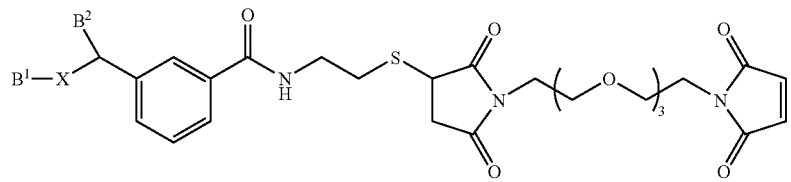

(VIII)

According to a further aspect of the invention there is provided a pharmaceutical composition which comprises a compound of formula (Ia) or (Ib) in association with one or more pharmaceutically acceptable carriers, excipients or diluents.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (Ia) or (Ib) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (Ia) or (Ib) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds according to the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds according to the present invention may be conveniently formulated as microionized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds according to the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of the present invention may be prepared by using methods analogous to those in the Examples provided herein.

Typically the compounds of formula (Ia) and (Ib) may be prepared by a process which comprises attachment of residue A to a compound of formula (VI) using procedures which are well known to the person skilled in the art. Where the compound of formula (VI) is used to produce the compound of formula (Ib) it will be appreciated that y=1.

The comb polymer moiety X may be prepared using any suitable polymerisation method known in the art. Suitable methods include living free radical polymerisation systems, see for example WO96/30421 and WO97/18247. Preferably the polymerisation method used is living radical polymerisation, as described in WO2004/113394, WO97/47661 and WO99/28362. Optionally, the polymerisation may also include a non-polymerisable scavenger agent, for example a disulfide.

Accordingly the present invention also provides a process for producing a comb-polymer comprising the steps of:
a) providing:
(i) (w+z) molar equivalents of a monomer
(ii) one molar equivalent of an initiator compound of formula (IX)

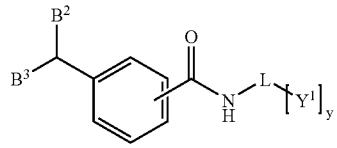

(IX)

wherein $B^3$ is a halogen and $Y^1$, L, $B^2$, y and (w+z) are as defined above;
(iii) a catalyst capable of catalysing the polymerisation of a plurality of the monomers to produce the comb polymer; and
b) causing the catalyst to catalyse, in combination with the initiator, the polymerisation of a plurality of the monomers (i) to produce the comb polymer.

The compound of formula (IX) is a novel compound and therefore constitutes a further feature of the present invention.

The compound of formula (IX) may be prepared by a process which comprises reacting a compound of formula (X) with a compound of formula (XI):

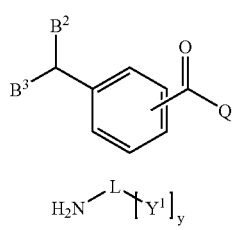

(X)

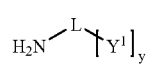

(XI)

wherein:
Q is a suitable leaving group. The leaving group Q is typically a halogen atom, e.g. chloro.

The monomer for use in step (i) of the process may be any monomer for use in the production of the 'backbone' of the comb to which effector and solubilising moieties may be subsequently attached. Examples of such monomers are:

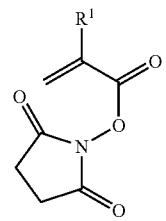

The invention also provides a process for producing a comb-polymer comprising effector molecules and optionally solubilising moieties said method further comprising step (c) in which the comb-polymer produced in step (b) is reacted with w equivalents of one or more effector molecules and z equivalents of one or more solubilising moieties wherein w and z are as set out above. The comb polymers produced by steps (b) and (c) of the above method are novel compounds and constitute a further feature of the present invention.

The invention also provides a process for producing a comb-polymer attached to at least one antibody or fragment thereof said process comprising attaching the comb polymer produced in step (b) or step (c) to at least one antibody or fragment thereof. The antibody-comb polymer conjugates produced by this process are novel compounds and constitute a further feature of the present invention.

Preferably the effector molecule moiety for use in step (c) has the formula $H_2N$-T-W where T and W are as defined above. Where present T preferably has the formula (V) as depicted above.

Preferably the solubilising moiety for use in step (c) has the formula $H_2N$-Z where Z is as defined above.

Preferably the solubilising moiety for use in step (c) has the formula:

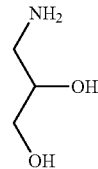

Alternatively, in the process of the present invention, the monomers for use in step (i) may already comprise the effector and/or solubilising moieties. Suitable monomers are well known in the art and will comprise Z, T and W moieties as defined above. In one example where the monomer comprises the effector moiety the monomer has the formula:

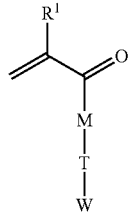

In one example where the monomer comprises the solubilising moiety the monomer has the formula:

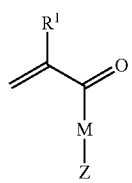

wherein $R^1$, M, T, W and Z are all as defined herein above.

The catalyst for use in step (a) of the process is any suitable catalyst known in the art. Examples of such catalysts have been provided in WO96/30421, WO97/18247, WO2004/113394, WO97/47661 and WO99/28362. Typically the catalyst is a transition metal salt where the transition metal has an oxidation state capable of being oxidised by one formal oxidation state plus an organodiimine. It will be appreciated that the catalyst may be a mixture. Suitably the catalyst is a mix of Cu(I)Cl and N-(n-propyl)-2-pyridyl methanimine (NMPI). Suitably the catalyst is used in the ratio initiator compound of formula (IX): Cu(I)Cl: NMPI of 1:1:2.

The amount of monomer required in step (i) of the process will depend on the number of units required in the polymer. For example, where a 15 unit polymer is required a 15:1 ratio of monomer to initiator may be used. Typical lengths of polymers are in the 1-300 unit range. In one preferred embodiment the unit length is 41.

Where a mixture of products is obtained from any of the processes described above for the preparation of compounds according to the invention, the desired product can be separated therefrom at an appropriate stage by conventional methods such as precipitation, dialysis, molecular weight filtration, gel permeation chromatography; cation or anion exchange; preparative HPLC; or column chromatography utilising, for example, silica and/or alumina in conjunction with an appropriate solvent system.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

The present invention also provides compounds consisting essentially of the following elements: a comb polymer suitable for the attachment of effector and optionally solubilising moieties and an antibody. Hence, in another aspect, the present invention provides novel compounds which are valuable intermediates for the attachment of effector molecules, solubilising moieties and antibodies or fragments thereof of which A is a residue. Thus, the invention also provides compounds of formula (XII):

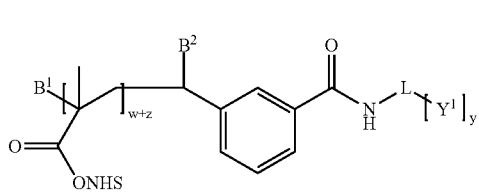

(XII)

Suitably the compound of formula (XII) has the formula (XIII)

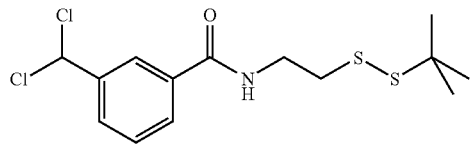

(XIII)

Suitably the compound of formula (XIII) has the formula (XIV)

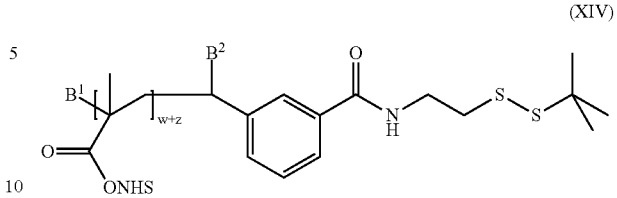

(XIV)

The compounds of formula XII, XIII and XIV are examples of the product of step (b) of the method described above.

The following non-limiting Examples illustrate the invention.

EXAMPLES

Initiator Synthesis

To a solution of 2-(t-butyldithio)-ethylamine hydrochloride (synthesis described in JACS, (1961), 83, 4414-17) (5.101 g, 0.025 mol) and diisopropylethyl amine (8.16 g, 0.063 mol) in dichloromethane (100 ml) at 0° C. was added over 10 minutes a solution of 3-(dichloromethyl)benzoyl chloride (5.929 g, 0.027 mol) in dichloromethane (20 ml). The solution was stirred at 0° C. for half an hour then allowed to warm to ambient temperature. The reaction was washed with 0.1 M HCl (100 ml) and water (100 ml), dried over magnesium sulphate and the solvent removed under vacuum. The resulting residue was purified by silica column chromatography eluting with 20% ethyl acetate 80% hexane to give the product as a colourless solid 8.52 g, 96%.

δH (d$_6$DMSO) 1.31 (9H, s), 2.92 (2H, t, J7.02 Hz), 3.54 (2H, q), 7.55 (1H, s), 7.57 (1H, t, J7.73 Hz), 7.78 (1H, dt, J8.37 Hz, J1.41 Hz), 7.89 (1H, dt, J7.89 Hz, J1.38 Hz), 8.12 (1H, t, J1.73 Hz), 8.79 (1H, t, J5.48 Hz). LCMS (ES+) 373.7 (MNa$^+$, 100%), 351.7 (MH+, 65%).

Polymerisation Procedure

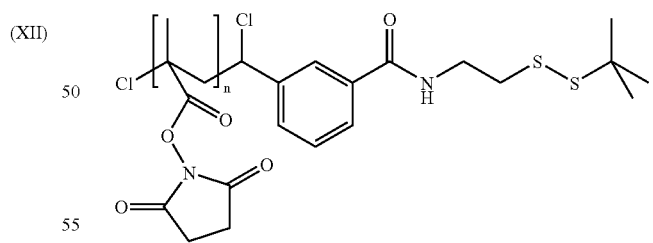

A typical synthesis is described for Polymer C

Reactions were carried out in Schlenk tubes sealed with rubber septa. Cu(I)Cl (0.16 g, 0.00164 mol) was added to the reaction vessel and subsequently deoxygenated by three consecutive vacuum, nitrogen purge cycles. To a second Schlenk tube Initiator (0.58 g, 0.00164 mol), N-hydroxy succinimide methacrylate (NHSMA) (15.0 g, 0.0819 mol), mesitylene (3.0 mL) and dimethyl sulphoxide (30 mL) were added and the mixture deoxygenated by purging with nitrogen for 30 minutes. Mesitylene (1 ml) is present as a standard marker to enable conversion calculations from $^1$H NMR. Once the solution was fully degassed N-(n-Propyl)-2-pyridylmethanimine (0.51 mL, 0.00328 mol) was added by pre-dried gas tight syringe to the Schlenk tube containing the copper chloride. The solution in the second Schlenk was then added to the catalyst containing Schlenk via a nitrogen purged stainless steel canular and the reaction mixture immediately placed in to a pre-heated oil bath set at 100° C. Samples were taken using deoxygenated gas tight syringe and immediately quenched by freezing in liquid nitrogen. The reaction was terminated by cooling rapidly and subsequent exposure to air. Polymers were purified by multiple precipitations from acetone using copious amounts of acetone to wash away dimethyl sulphoxide.

Polymer A

Cu(I)Cl 0.54 g, 0.00546 mol, Initiator 1.92 g, 0.00546 mol, NHSMA 15.0 g, 0.0819 mol DMSO 30 mL, Mesitylene 3 mL, N-(n-propyl)-2-pyridylmethanimine 1.70 mL, 0.0109 mol Polymer B Cu(I)Cl 0.20 g, 0.00204 mol, Initiator 0.72 g, 0.00204 mol, NHSMA 15.0 g, 0.0819 mol, DMSO 30 mL, Mesitylene 3 mL, N-(n-propyl)-2-pyridylmethanimine 0.64 mL, 0.00409 mol Polymer C Cu(I)Cl 0.16 g, 0.00164 mol, Initiator 0.58 g, 0.00164 mol, NHSMA 15.0 g, 0.0819 mol, DMSO 30 mL, Mesitylene 1 mL, N-(n-propyl)-2-pyridylmethanimine 0.51 mL, 0.00328 mol Polymer D Cu(I)Cl 0.08 g, 0.00082 mol, Initiator 0.29 g, 0.00082 mol, NHSMA 15.0 g, 0.0819 mol DMSO 30 mL, Mesitylene 1 mL, N-(n-propyl)-2-pyridylmethanimine 0.26 mL, 0.00164 mol Polymer E Cu(I)Cl 0.07 g, 0.00073 mol, Initiator 0.26 g, 0.00073 mol, NHSMA 20.0 g, 0.1092 mol, DMSO 40 mL, Mesitylene 1 mL, N-(n-propyl)-2-pyridylmethanimine 0.23 mL, 0.00146 mol Polymer F Cu(I)Cl 0.036 g, 0.00036 mol, Initiator 0.13 g, 0.00036 mol, NHSMA 20.0 g, 0.1092 mol, DMSO 40 mL, Mesitylene 1 mL, N-(n-propyl)-2-pyridylmethanimine 0.11 mL, 0.00073 mol

| Polymer | Time (Mins) | Conversion | DP (1H NMR) | DP (GPC) | PDI (GPC) |
|---|---|---|---|---|---|
| A | 40 | 67% | 5 | 17 | 1.19 |
| B | 50 | 66% | 13 | 24 | 1.31 |
| C | 60 | 78% | 41 | 100 | 1.19 |
| D | 60 | 69% | 96 | 110 | 1.20 |
| E | 60 | 72% | 164 | 175 | 1.34 |
| F | 120 | 64% | 262 | 195 | 1.31 |

Intermediate 1a

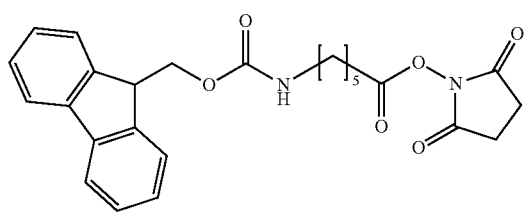

N,N-Diisopropylethylamine (1.8 mL, 10.35 mmol) was added to a stirred mixture of N-Fmoc-6-aminocaproic acid (2 g, 5.67 mmol) (from Bachem), N-hydroxysuccinimide (0.78 g, 6.78 mmol) and dicyclohexylcarbodiimide (1.4 g, 6.8 mmol) in DCM (30 mL) and stirred for 2 h. The reaction mixture was filtered through celite and concentrated by rotary evaporation. The product was crystallised from ether, filtered, washed several times with ether and dried to give 2.5 g (98%). ¹H.n.m.r. (CDCl₃), δ 7.75-7.70 (d, 2H), 7.64-7.50 (d, 2H), 7.4 (dd, 1H), 7.3 (dd, 1H), 4.38-5.0 (b, 1H), 4.30-4.42 (m, 2H), 4.20-4.30 (m, 1H), 3.45 (ddd, 1H), 3.10-3.25 (m, 2H), 2.70-2.85 (b, 4H), 2.50-2.65 (m, 3H). LCMS, (ES+), 449.2 (MH⁺), 473 (MNa⁺).

Intermediate 1b

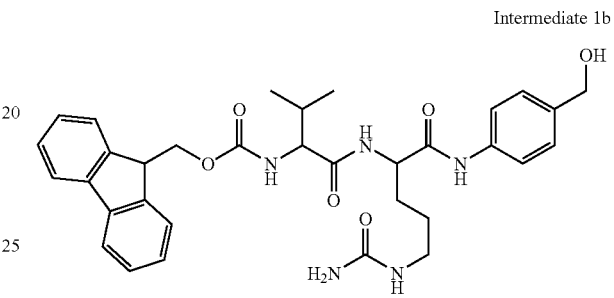

A mixture of Fmoc-Val-Cit (5.32 g, 10.70 mmol) (prepared as described in Bioconjugate Chem. 2002, 13, 855-869), EEDQ (5.32 g, 21.54 mmol), and p-aminobenzyl alcohol (2.65 g, 21.50 mmol) in DCM-MeOH, 2:1 (150 mL) was stirred overnight. The reaction mixture was diluted with ethyl acetate and the solid product triturated, filtered, washed several times with ethyl acetate, then DCM and dried to give 5.05 (78%). ¹H.n.m.r. (DMSO-d₆), δ9.97 (bs, 1H), 8.10 (d, 1H), 7.90 (d, 2H), 7.75 (t, 2H), 7.55 (d, 2H), 7.42 (t, 3H), 7.33 (t, 2H), 7.24 (d, 2H), 5.96 (b, 1H), 5.40 (bs, 2H), 5.09 (t, 1H), 4.43 (m, 3H), 4.2-4.35 (m, 3H), 3.94 (t, 1H), 2.93-3.04 (m, 2H), 1.99 (b, 1H), 1.58-1.75 (m, 2H), 1.40-1.50 (m, 2H), 0.87 (m, 6H). LCMS (ES+), 603 (MH⁺), 625 (MNa⁺).

Intermediate 1c

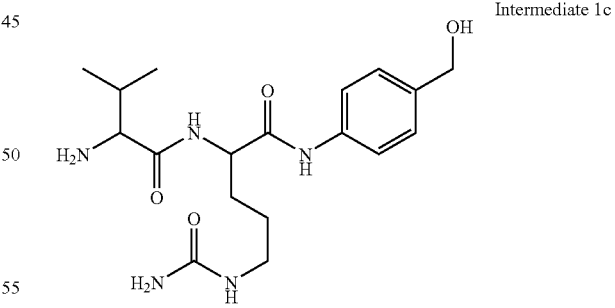

A solution of 20% piperidine in DMF (3 mL) was added to a stirred solution of Intermediate 1b (1 g, 1.66 mmol) in DMF (10 mL) and the mixture stirred for 2 h. The solvent was removed and the residue partitioned between water and DCM. The aqueous layer was washed three times with DCM then concentrated and freeze-dried to give 0.62 g (98%). ¹H.n.m.r. (DMSO-d₆), δ10.03 (s, 1H), 8.14 (b, 1H), 7.24 (d, 2H), 5.97 (t, 1H), 5.40 (b, 2H), 5.10 (b, 1H), 4.43 (b, 3H), 2.30 (b, 1H), 2.92-3.12 (m, 3H), 1.95 (m, 2H), 1.50-1.78 (m, 4H), 0.89 (d, 3H), 0.79 (d, 3H). LC/MS 381 (MH⁺), 403 (MNa⁺).

Intermediate 1d

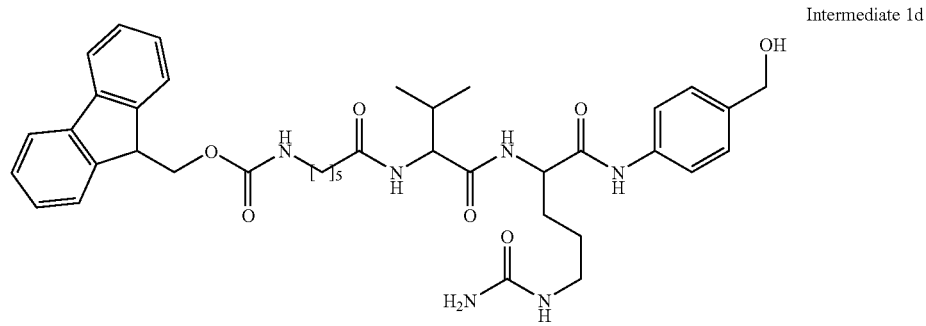

Intermediate 1c (0.5 g, 1.316 mmol) was dissolved in DMF (5 mL), stirred at room temperature and Intermediate 1a (0.592 g, 1.316 mmol) and DIPEA were added sequentially. The reaction mixture was stirred for 3 h and the mixture poured with stirring into ice-water and the precipitated product filtered off, washed several times with water and dried to give 0.73 g (78%). $^1$H.n.m.r. (DMSO-$d_6$), δ9.90 (s, 1H), 8.05 (d, 1H), 7.88 (d, 2H), 7.80 (d, 1H), 7.69 (d, 2H), 7.58 (d, 2H), 7.45 (t, 2H), 7.24 (d, 2H), 5.96 (t, 1H), 5.4 (b, 2H), 5.10 (t, 1H), 4.15-4.47 (m, 7H), 2.40-3.07 (m, 4H), 2.16 (m, 2H), 1.96 (m, 1H), 0.96-1.77 (m), 0.81 (m, 7H). LCMS (ES+), 715 (MH$^+$) 737 (MNa$^+$).

Intermediate 1e

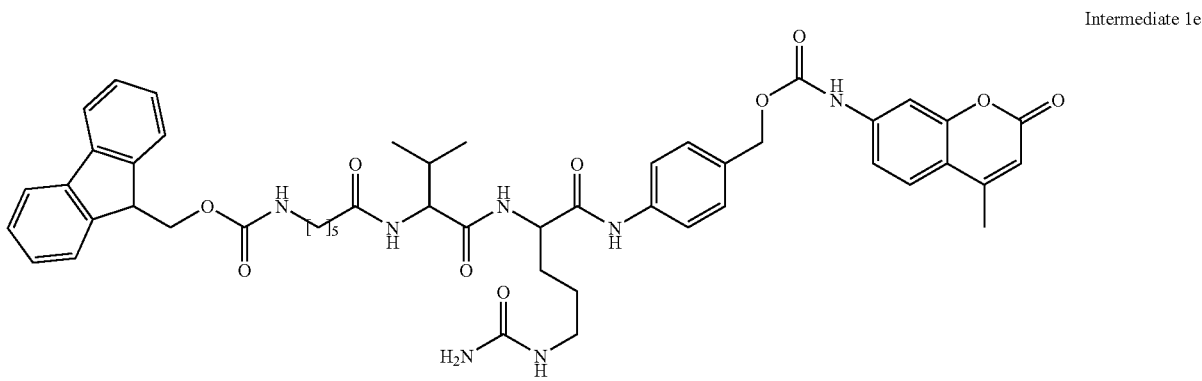

Intermediate 1 d (0.5 g, 0.70 mmol) was dissolved in DMF (5 mL) by warming the suspension. The clear solution was then stirred under $N_2$ and 7-Isocyanato-4-methyl-chromen-2-one (0.22 g, 1.09 mmol) (prepared as described in Anal. Biochem., 1992, 200, 400-404) was added and the reaction mixture stirred under $N_2$ in the dark overnight. The solidified reaction mixture was thoroughly digested in DCM, filtered, washed several times with DCM, then ether, and dried to give 0.57 g (90%). $^1$H.n.m.r. (DMSO-$d_6$), δ10.27 (s, 1H), 10.22 (s, 1H), 7.22-8.04 (m, 22H), 6.23 (s, 2H), 5.98 (t, 1H), 5.39 (s, 2H), 5.13 (s, 2H), 4.18-4.44 (m, 6H), 2.87-3.20 (m), 2.38 (s, 3H), 2.40 (s, 3H), 1.25-2.23 (m), 0.85 (m, 6H). LCMS (ES+), 938 (MNa$^+$).

Effector Species (I)

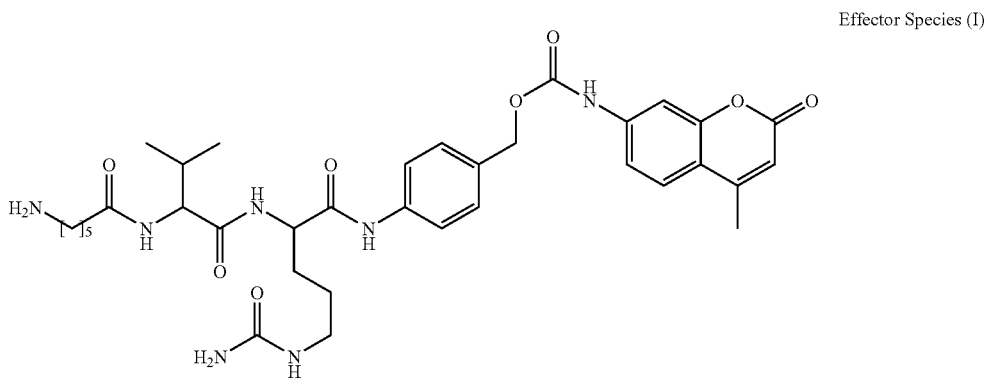

Intermediate 1e (0.57 g, 0.62 mmol) was suspended in DMF (10 mL) and a 20% piperidine in DMF solution (3 mL) added and the mixture was stirred at room temperature for 2.5 h during which the starting material gradually dissolved to form a clear solution. The mixture was rotary evaporated under reduced pressure and the residual crude was triturated in EtOAc-MeOH, 9:1, filtered, washed with same solvent and dried to give 0.42 g (97%). $^1$H.n.m.r. (DMSO-$d_6$), δ10.00 (s, 2H), 8.07 (d, 2H), 7.80 (d, 2H), 7.34-7.70 (m, 8H), 6.24 (m, 2H), 5.98 (t, 1H), 5.4 (s, 2H), 5.12 (s, 2H), 4.40 (m, 1H), 3.01 (m), 2.38 (s), 2.4 (s), 2.1-2.2 (m), 1.9-2.04 (m), 1.15-1.78 (m), 0.8-0.9 (m). LCMS (ES+), 694 (MH$^+$).

followed by DMAP (170 mg, 1.39 mmol) that was previously dried in vacuum over sodium hydroxide and the reaction mixture was stirred for 2.5 h. TLC (DCM-MeOH, 9:1) showed formation of the product and some unreacted starting material peptide. The semisolid mixture was poured into ice water and the yellow solid was collected by filtration, washed several times with ice water and dried by air suction. LC/MS of the crude showed the ratio of the product to the unreacted peptide was 2:1. It was dissolved in DMF and the required product was separated using preparative TLC (1 mm silica gel thickness) in DCM-MeOH, 9:1 to give the product as yellow

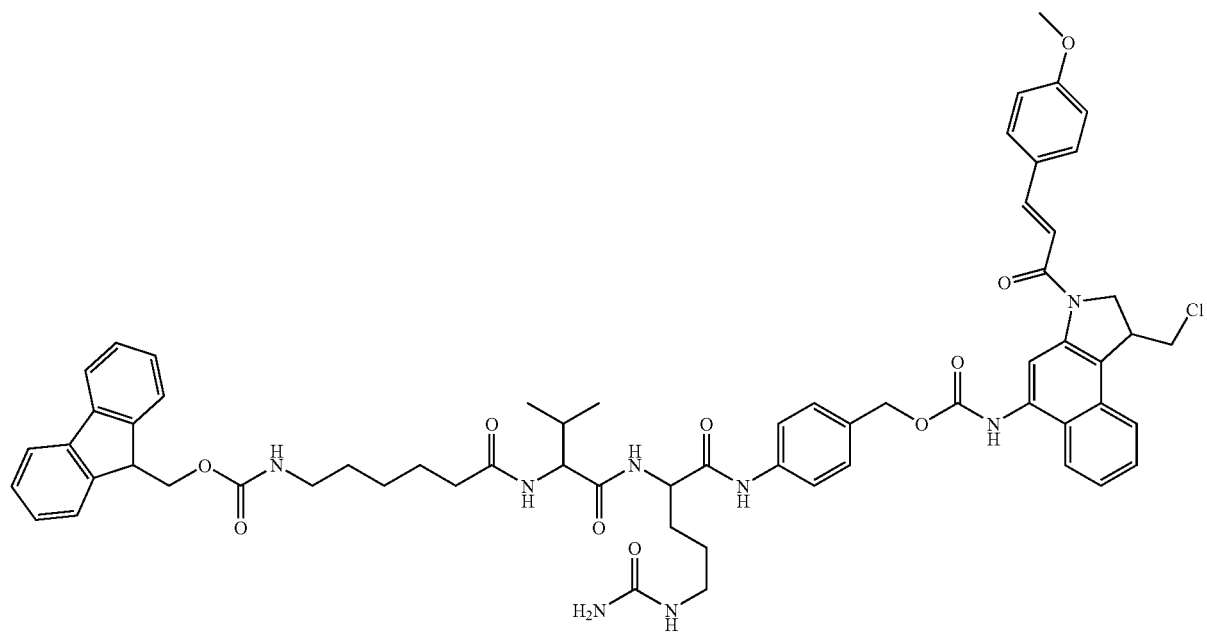

Intermediate 2a 1-(Chloromethyl)-3-[(2E)-3-(4-methoxyphenyl)-2-propenoyl]-1,2-dihydro-3H-benzo[e]indol-5-amine (55 mg, 0.14 mmol), (prepared as described in WO03097635) in acetonitrile was treated with 20% phosgene in toluene (1.5 mL) for 1.5 h. The resulting clear solution was evaporated to dryness under reduced pressure, co-evaporated twice with anhydrous DCM and left on the vacuum line for 1 h. The crude product was re-dissolved in acetonitrile (4 mL) and added dropwise to a solution of 1d (100 mg, 0.14 mmol) in DMF (1.5 mL)

solid (60 mg, 38%). $^1$H.n.m.r. (DMSO-$d_6$), δ9.97 (bs, 1H), 9.59 (b, 1H), 8.11 (d, 1H), 8.01 (d, 1H), 7.86 (d, 1H), 7.73-7.81 (m, 2H), 7.62-7.73 (m, 3H), 7.54-7.62 (m, 3H), 7.4-7.46 (t, 1H), 7.25-7.34 (m, 3H), 7.06-7.24 (m, 3H), 6.88-6.96 (d, 2H), 6.15 (b, 1H), 5.48 (s, 2H), 5.06 (s, 21H), 4.50 (m, 2H), 4.4.08-4.25 (m, 4H), 3.75 (s, 3H), 3.10 (b, 1H), 2.9-3.03 (m, 3H), 2.18 (m, 2H), 2.04 (m, 2H), 1.77 (m, 2H), 1.55 (m, 2H), 1.50 (m, 2H), 1.38 (m), 1.38 (m, 2H), 1.12-1.32 (m, 6H), 0.72-0.85 (m, 6H). LC/MS $R_T$ 3.63 min, m/z 1133 (M)$^+$.

Effector Species (II)

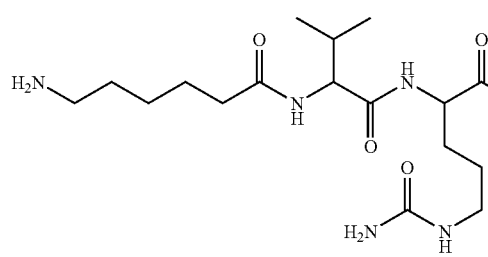

20% Piperidine in DMF (1.5 mL) was added to a solution of 2a (60 mg, 52.98 mmol) in DMF (3 mL) and the reaction mixture was stirred for 2 h when tlc (DCM-MeOH, 9:1) showed full consumption of the starting material. All volatiles were removed by rotary evaporation and the residue was digested in DCM-ether, 1:1, filtered, washed several times with the same solvent and dried to give 45 mg (93%). $^1$H.n.m.r. (DMSO-$d_6$), $\delta$10.0 (bs, 1H), 8.68 (b, 1H), 8.10 (m, 1H), 8.02 (d, 1H), 7.92 (d, 1H), 7.80 (m, 3H), 7.66 (m, 3H), 7.56 (t, 1H), 7.42 (m, 3H), 7.10 (d, 1H), 7.02 (d, 2H), 6.00 (b, 1H), 5.42 (s, 2H), 5.14 (s, 2H), 4.53 (m, 2H), 4.39 (m, 2H), 4.19 (t, 1H), 4.03 (m, 1H), 3.93 (m, 1H), 3.83 (s, 3H), 2.90-3.06 (m, 3H), 2.55 (m, 2H), 2.18 (m, 2H), 2.0 (m, 1H), 1.72 (m, 1H), 1.63 (m, 1H), 1.50 (m, 3H), 1.38 (m, 2H), 1.23 (m, 2H), 0.8-0.88 (m, 6H). LC/MS $R_T$ 2.57 min, m/z 911 (M)$^+$.

Intermediate 3a

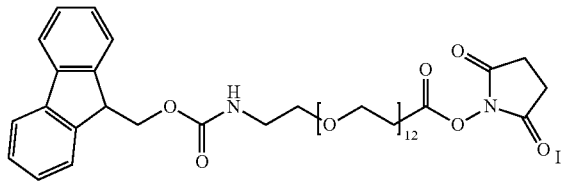

To a solution of N-Fmoc-amido-dPEG™$_{12}$ Acid (1.0 g, 1.19 mmol) from Quanta Biodesign in DCM (10 mL) was added N-hydroxysuccinimide (150 mg, 1.3 mmol), DCC (270 mg, 1.31 mmol), and DIPEA (517 µL, 2.97 mml) and the reaction mixture was stirred overnight. LC/MS showed only 50% reaction and it did not improve upon the addition of more reagents and prolonged stirring. Therefore, the solid was filtered-off and the filtrate was washed with bicarbonate solution, dried (MgSO4) and concentrated. Column chromatography using DCM-MeOH, 20:1 furnished pure product (0.355 g, 32% and 60% based on recovered starting material). Then the column was eluted with MeOH to recover the unreacted starting material (0.47 g). $^1$H.n.m.r. (CDCl$_3$), $\delta$7.76 (d, 2H), 7.61 (d, 2H), 7.38 (dd, 2H), 7.31 (dd, 2H), 5.48 (b, 1H), 4.41 (d, 2H), 4.24 (m, 1H), 3.85 (t, 2H), 3.65 (b, PEG), 3.39 (b, 2H), 2.87 (t, 1H), 2.84 (b, 3H), 1.74 (b, 4H). LC/MS $R_T$ 3.17 min, m/z 937 (M)$^+$, 938 (M+1)$^+$.

Intermediate 3b

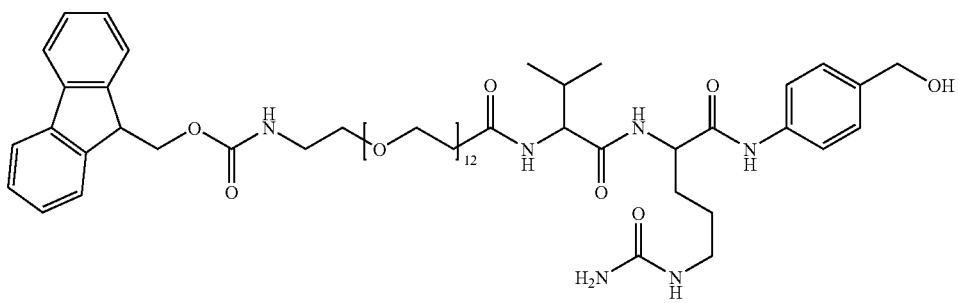

1c (0.144 g, 0.379 mmol) was added to a solution of 3a (0.355 g, 0.379 mmol) in DMF (3 mL) followed by DIPEA (165 µL, 0.95 mmol) and the reaction mixture was stirred overnight. LC/MS revealed that the basic medium had caused the hydrolysis of the Fmoc-protecting group from some of the product to give a mixture of the required product together with some unprotected amine. Ice water was added and a small amount of white solid was filtered off and the filtrate was freeze-dried. The semi solid was taken up in water-acetonitrile, 1:1 (10 mL) and stirred with sodium bicarbonate (50 mg, 0.6 mmol) and Fmoc-O-Su (150 mg, 0.45 mmol) for 20 min. LC/MS showed completion of the reaction to give one major product. Any insoluble material was removed by filtration and the filtrate was concentrated and loaded to C18 column eluting first with water, then 20%, 40%, 60%, and 80% MeOH. The required product was eluted in the 80% MeOH fractions; these were concentrated and freeze dried to give 220 mg, (48%). $^1$H.n.m.r. (MeOD), $\delta$7.82 (d, 2H), 7.67 (d, 2H), 7.59 (d, 2H), 7.42 (m, 2H), 7.33 (m, 2H), 4.55 (m, 1H), 4.38 (d, 2H), 4.22 (m, 2H), 3.78 (m, 2H), 3.6-3.68 (b, PEG), 3.54 (m, 2H), 2.56 (m, 2H), 2.14 (m, 1H), 1.93 (m, 1H), 1.8 (m, 1H), 1.62 (m, 2H), 1.00 (m, 6H). LC/MS $R_T$ 2.9 min, m/z 1202 (M)$^+$.

Intermediate 3c

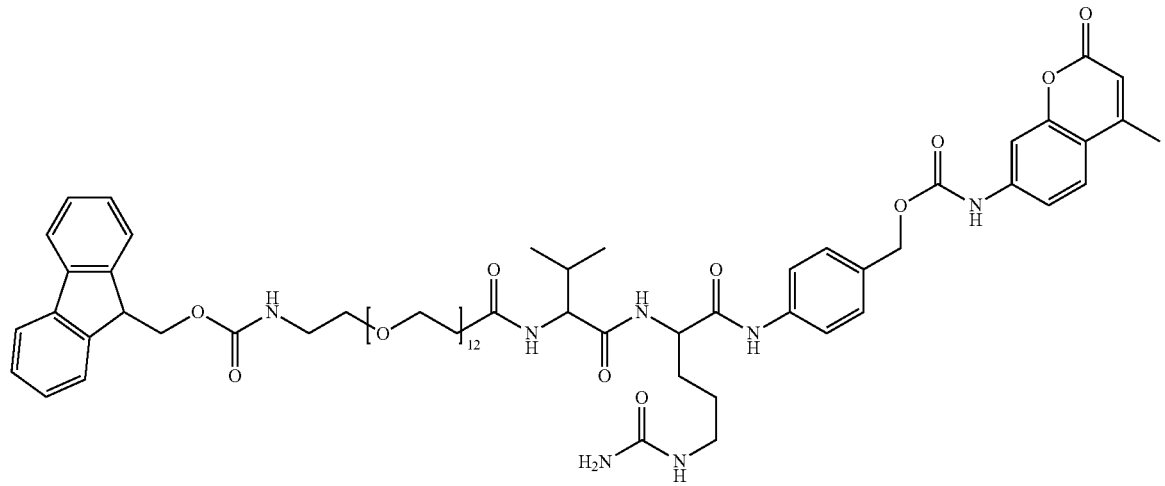

A solution of 3b (164 mg, 0.136 mmol) in DMF (2 mL) was stirred under $N_2$ and 7-isocyanato-4-methyl-chromen-2-one (55 mg, 0.273 mmol) (prepared as described in Anal. Biochem., 1992, 200, 400-404) was added and stirred at 45° C. for 3 h. LC/MS showed about 60% reaction and therefore more 7-isocyanato-4-methyl-chromen-2-one (30 mg, 0.149 mmol) was added and the reaction mixture was stirred at the same temperature for a further 2 h. LC/MS showed only a trace of unreacted 3b, solvent was removed by rotary evaporation and the residue was triturated in EtOAc-MeOH, 4:1, filtered and washed several times with the same solvent and dried to give 180 mg (94%). $^1$H.n.m.r. (300 MHz, DMSO-d$_6$), $\delta$ 9.65 (b, 1H), 7.80-7.96 (m, 1H), 7.22-7.78 (m, 9H), 6.23 (s, 1H), 5.39 (s, 1H), 5.13 (s, 1H), 4.16-4.50 (m, 2H), 4.0-4.12 (m, 1H), 3.38-3.88 (m, includes PEG), 3.08-3.21 (m, 1H), 2.9-3.9 (m, 1H), 2.40 (s, 3H), 1.21-1.84 (m, 3H), 0.85 (t, 3H). LC/MS $R_T$ 3.154 min, m/z 1402 (M)$^+$, 1425 (M+Na)$^+$.

Effector Species (III)

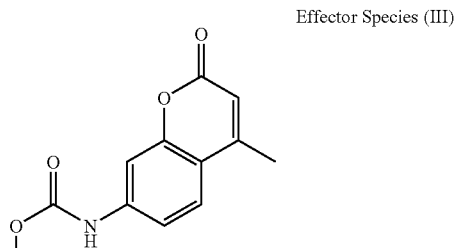
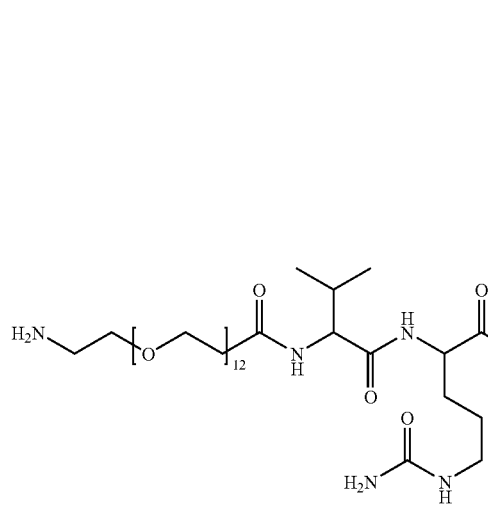

3c (60 mg, 42.8 mmol) was suspended in DMF (1 mL) and 20% piperidine in DMF solution (1 mL) was added to form a clear solution, which was stirred for 1.5 h. The reaction mixture was evaporated to dryness, the residue was triturated in EtOAc and the solid was filtered, washed several times with EtOAc and dried in vacuum to give 40 mg (79%). $^1$H.n.m.r. (DMSO-d$_6$), δ 10.0 (s, 1H), 8.11 (d, 1H), 7.87 (d, 1H), 7.70 (d, 1H), 7.64 (d, 2H), 7.56 (d, 1H), 7.38-7.43 (m, 3H), 6.24 (s, 1H), 5.98 (m, 1H), 5.41 (b, 2H), 5.13 (b, 2H), 4.39 (m, 1H), 4.23 (m, 1H), 3.39-3.55 m, includes PEG), 3.33 (m, 1H), 2.89-3.1 (m, 2H), 2.58 (m, 2H), 2.40 (s, 3H), 1.98 (m, 1H), 1.74 (m, 1H), 1.61 (m, 1H), 1.31-1.52 M, 2H), 0.57-0.69 (m, 3H). LC/MS R$_T$ 2.40 min., 77/z 1181 (M+1)$^+$.

acetonitrile (3 mL) under nitrogen followed by DMAP (360 mg, 2.95 mmol, 32 eq.). DMF (200 µL) was added to obtain clear solution, which was then stirred in the dark under nitrogen for 0.5 h. LC/MS revealed that the required product had been formed but it had lost the Fmoc-protecting group to give the free terminal amine (R$_T$=2.925 min) compared to R$_T$=3.377 min for the protected amino product. The reaction mixture was first concentrated to remove excess acetonitrile then diluted with water and loaded to C18 column eluted first with water, then MeOH-water, 1:1, which removed all DMAP then the required product was eluted using 2:1 ratio. These fractions were concentrated and freeze dried to give 75 mg (58%). $^1$H.n.m.r. (DMSO-d$_6$), δ 9.88 (s, 1H), 8.99 (b, 1H), Effector Species (IV)

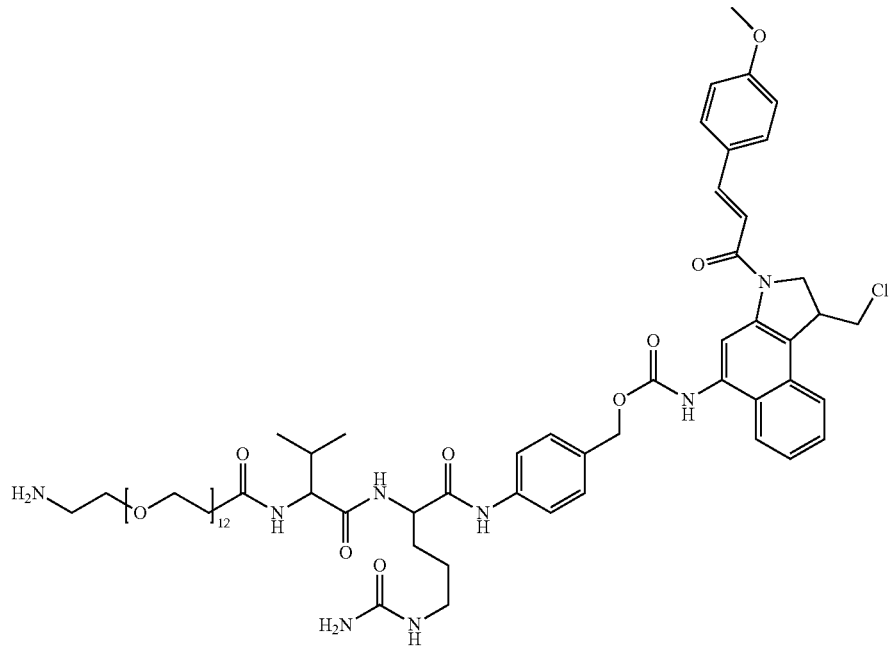

1-(Chloromethyl)-3-[(2E)-3-(4-methoxyphenyl)-2-propenoyl]-1,2-dihydro-3H-benzo[e]indol-5-amine (36 mg, 91.72 µmol), (prepared as described in WO03097635) in acetonitrile was treated with 20% solution of phosgene in toluene (600 µL) for 4 h then it was evaporated to dryness, co-evaporated twice with acetonitrile and left on the vacuum line for 0.5 h. The resulting crude was dissolved in acetonitrile (3 mL) and added to another solution of 3b (112 mg, 93.2 µmol) in 8.65 (b, 1H), 8.07-8.11 (m, 2H), 7.78 (d, 1H), 7.66 (m, 1H), 7.53-7.68 (m, 2H), 7.37-7.46 (m, 2H), 7.29-7.35 (m, 2H), 7.00-7.02 (m, 2H), 6.57-6.59 (m, 1H), 6.58 (m, 1H), 6.01 (m, 1H), 5.4 (b, 1H), 4.18-4.47 (m, 4H), 4.00 (m, 1H), 3.92 (m, 1H), 3.81 (s, 3H), 3.28-3.63 (m, including PEG), 2.40 (m, 1H), 1.95 (m, 1H), 1.7 (m, 1H), 1.62 (m, 1H), 1.33-1.52 (m, 2H), 0.76-0.87 (m, 6H). LC/MS R$_T$ 2.906 min, m/z 1398 (M)$^+$.

Intermediate 5a

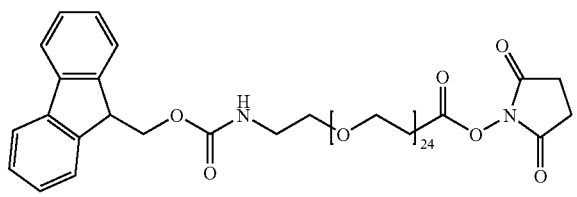

A mixture of N-Fmoc-amido-dPEG™$_{24}$ acid (100 mg, 73.1 mmol) purchased from Quanta Biodesign, N-hydroxysuccinimide (18 mg, 0.156 mmol), DCC (33.1 mg, 0.16 mmol) and DIPEA (65 μL) in DCM (2 mL) was stirred overnight. LC/MS showed a new product ($R_T$ 3.042 min) compared to the starting material acid ($R_T$ 2.962 min). The solid was filtered off and the filtrate was concentrated and triturated several times with ether and dried to give 210 mg (93%). $^1$H.n.m.r. (CDCl$_3$), δ 7.77 (d, 2H), 7.61 (d, 2H), 7.39 (t, 2H), 7.31 (t, 2H), 5.48 (b, 1H), 4.42 (m, 2H), 4.23 (m, 2H), 3.85 (m, 2H), 3.64 (s, PEG), 2.90 (m, 2H), 2.84 (m, 4H). LC/MS $R_T$ 3.042 min, m/z 1466 (M+1)$^+$.

Intermediate 5b

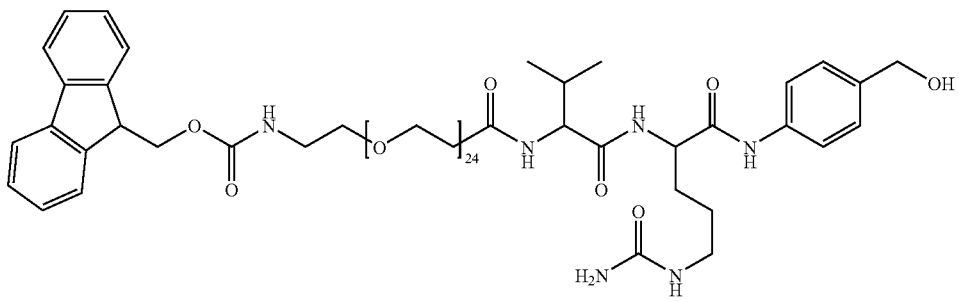

A solution of 1c (27.2 mg, 71.58 μmol) in DMF (1.5 mL) was added to 5a (105 mg, 71.67 μmol) followed by DIPEA (50 μL, 287.6 μmol) and stirred overnight. LC/MS showed the formation of the product ($R_T$ 2.881 min) and some unreacted starting material. The reaction mixture was concentrated and the product was isolated by reverse phase chromatography as described for the 3b to give 68 mg (55%). $^1$H.n.m.r. (DMSO-d$_6$), δ 9.89 (s, 1H), 8.08 (b, 1H), 7.84-7.90 (m, 4H), 7.68 (d, 1H), 7.55 (d, 2H), 7.42 (m, 2H), 7.33 (m, 2H), 6.97 (m, 1H), 5.40 (b, 2H), 4.21-5.40 (m, 6H), 3.22-3.71 (m, includes PEG), 3.15 (m, 1H), 2.9-3.08 (m, 2H), 2.4 (m, 2H), 1.96 (m, 1H), 1.72 (m, 1H), 1.62 (m, 1H), 0.76-0.9 (m, 6H). LC/MS $R_T$ 2.879 min, m/z 1731 (M+1)$^+$.

Effector Species (V)

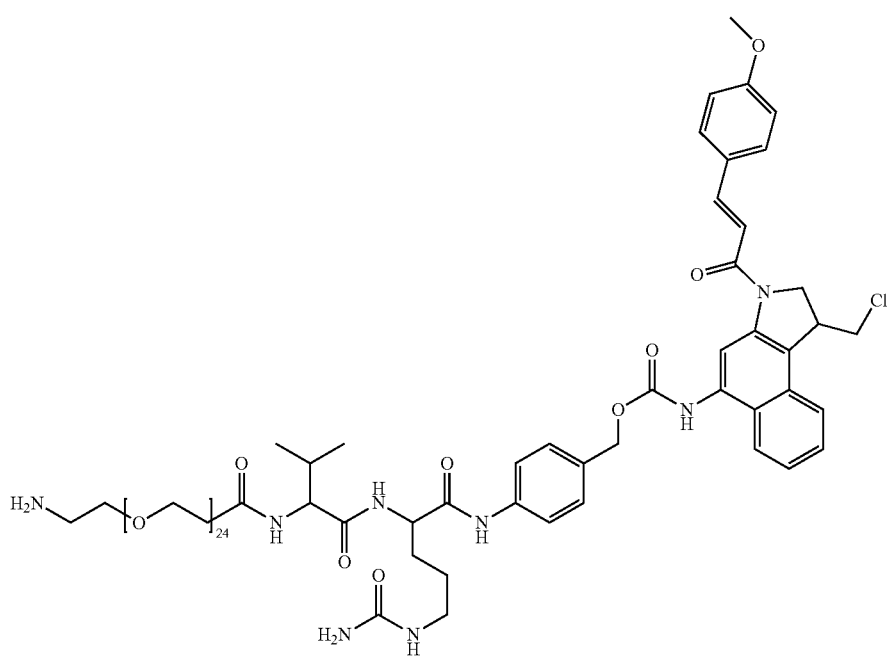

1-(Chloromethyl)-3-[(2E)-3-(4-methoxyphenyl)-2-propenoyl]-1,2-dihydro-3H-benzo[e]indol-5-amine (20 mg, 50.96 µmol), (prepared as described in WO03097635) in acetonitrile (1.5 mL) was treated with 20% solution of phosgene in toluene (100 µL) for 4 h, then concentrated by rotary evaporation and left on the vacuum line for 0.5 h. The crude product was re-dissolved in acetonitrile (1 mL) and added under nitrogen to another solution of the 5b (60 mg, 34.7 µmol) in acetonitrile (1.5 mL) followed by DMAP (212 mg, 1.738 mmol). The reaction mixture was stirred in the dark and monitored by LC/MS which showed that the formation of the product was followed by loss of the Fmoc-protecting group to give a mixture of the Fmoc-protected and unprotected amine. Therefore the reaction mixture was concentrated and treated with 20% piperidine in DMF for 3 h. It was then concentrated again and the crude was subjected to reverse phase column chromatography eluting with water-MeOH to give the product (12 mg, 18%). $^1$H.n.m.r. (CDCl$_3$), δ 9.25 (s, 1H), 8.14 (b, 1H), 7.15-8.05 (m, 15H), 6.04 (b, 1H), 5.17 (m, 1H), 3.94-4.75 (m, 6H), 3.86 (s, 3H), 3.45-3.72 (m, includes PEG), 3.25 (m, 1H), 2.6 (m, 2H), 2.25 (m, 2H), 1.96 (m, 1H), 1.72 (m, 1H), 1.62 (m, 1H), 0.76-0.9 (m, 6H). LC/MS R$_T$ 2.908 min, m/z 1927 (M)$^+$.

Intermediate 6b

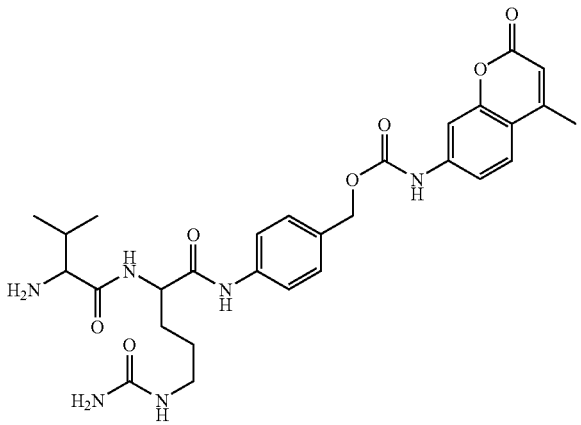

Intermediate 6a

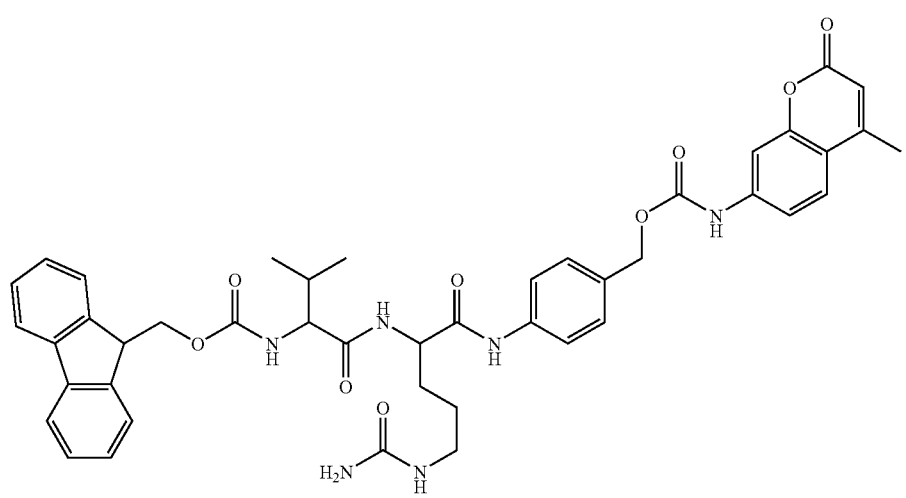

To a solution of 1b (250 mg, 0.415 mmol) in DMF (2.5 mL) was added 7-isocyanato-4-methyl-chromen-2-one (167 mg, 0.83 mmol) (prepared as described in Anal. Biochem., 1992, 200, 400-404) and the reaction mixture was stirred at 50° C. until LC/MS indicated completion of the reaction (2 h). Solvent was removed under vacuum and the crude was subjected to column chromatography using DCM-MeOH, 9:1 to give the product (109 mg, 33%. $^1$H.n.m.r. (DMSO-d$_6$), δ 10.26 (s, 1H), 10.10 (s, 1H), 8.11 (m, 1H), 7.89 (m, 2H), 7.56-7.76 (m, 5H), 7.29-7.46 (m, 8H), 6.24 (s, 1H), 6.00 (m, 1H), 5.41 (s, 1H), 5.14 (s, 1H), 4.44 (m, 1H), 4.23-4.41 (m, 3H), 3.93 (m, 1H), 2.85-3.18 (m, 2H), 2.38 (s, 3H), 2.00 (m, 1H), 1.68 (m, 1H), 1.62 (m, 1H), 1.32-1.52 (m, 2H), 0.80-0.9 (m, 6H). LC/MS R$_T$ 3.329 min, m/z 803 (M)$^+$, 804 (M+1)$^+$.

6a (105 mg, 0.131 mmol) was suspended in DMF (2 mL) and a 20% solution of piperidine in DMF (1 mL) was added and stirred for 1 h. The clear solution was rotary evaporated to dryness and the residual crude was triturated in DCM, filtered, washed repeatedly with DCM and dried to give 69 mg (91%). $^1$H.n.m.r. (DMSO-d$_6$), δ 10.26 (s, 1H), 10.15 (s, 1H), 7.62-7.71 (m, 3H), 7.39-7.42 (m, 2H), 6.24 (b, 1H), 5.40 (b, 1H), 5.14 (b, 1H), 2.89-3.18 (m, 3H), 2.41 (s, 3H), 1.98 (m, 1H), 1.66 (m, 1H), 1.59 (m, 1H), 1.40 (m, 2H), 0.90 (d, 3H), 0.79 (d, 3H). LC/MS R$_T$ 2.339 min, m/z 581 (M)$^+$, 582 (M+1)$^+$.

Intermediate 6c

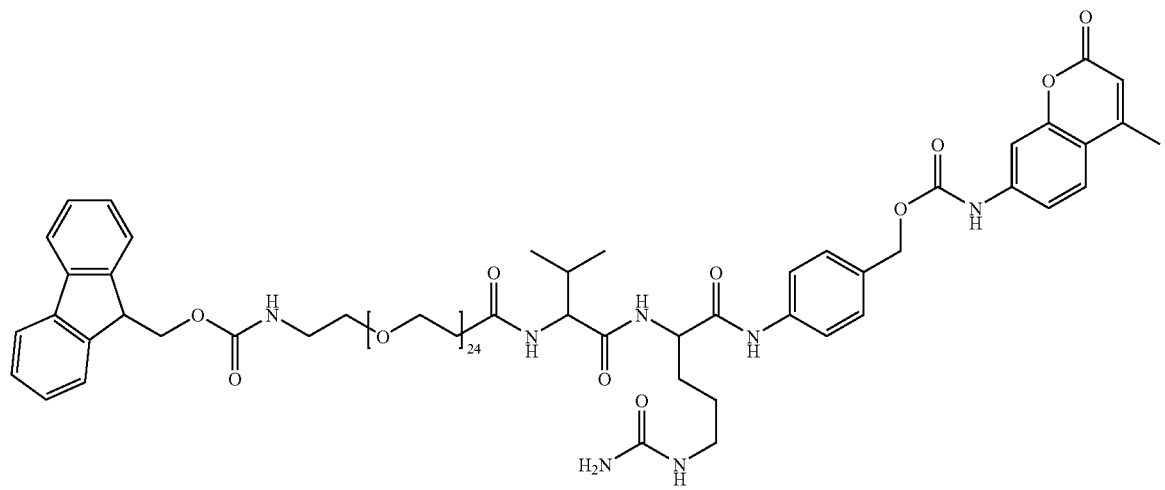

A mixture of 5a (100 mg, 68.26 mmol), 6b (39.7 mg, 68.31 mmol) and DIPEA (30 µL, 172.61 mol) in DMF (1.5 mL) was stirred overnight when LC/MS showed completion of the reaction. All volatiles were removed by rotary evaporation and the residue was triturated several times with ether-DCM, 9:1, filtered, washed with the same solvent and dried to give (80 mg, 54%). $^1$H.n.m.r. (DMSO-$d_6$), δ 10.25 (s, 1H), 10.01 (s, 1H), 8.11 (m, 1H), 7.89 (m, 2H), 7.63-7.72 (m, 4H), 7.31-7.42 (m, 5H), 6.24 (s, 1H), 6.00 (m, 1H), 5.41 (s, 1H), 5.13 (s, 1H), 4.13-4.40 (m, 3H), 3.50-3.72 (m, includes PEG), 3.13-3.33 (m, 2H), 2.89-3.13 (m, 1H), 2.41 (s, 3H), 2.00 (m, 1H), 1.19-1.80 (m, 5H), 0.80 (m, 6H). LC/MS $R_T$ 3.052 min, m/z 581 (M)$^+$, 582 (M+1)$^+$.

Effector Species (VI)

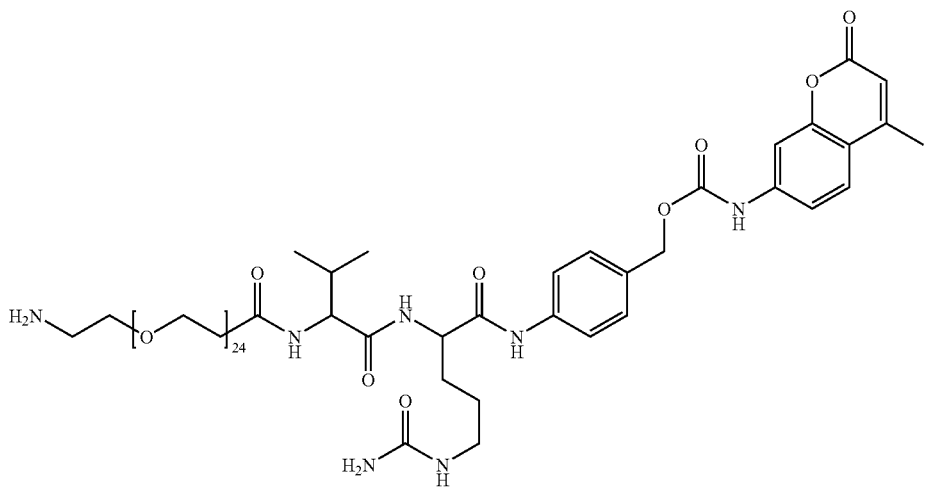

6c (74 mg, 34.24 µmol) in DMF (2 mL) was treated with 20% piperidine solution in DMF (2 mL) for 2 h. The solution was evaporated to dryness and repeatedly triturated in ether-DCM, 4:1, filtered, washed with the same solvent and dried to give 38 mg (57%). $^1$H.n.m.r. (DMSO-$d_6$), δ 10.25 (s, 1H), 10.02 (s, 1H), 8.11 (m, 1H), 7.88 (m, 1H), 7.55-7.71 (m, 6H), 7.35-7.49 (m, 5H), 6.24 (s, 1H), 6.00 (m, 1H), 5.42 (s, 1H), 5.13 (s, 1H), 4.38 (m, 1H), 4.21 (m, 1H), 3.10-4.18 (m, includes PEG), 3.00 (m, 2H), 2.40 (s, 3H), 1.98 (m, 1H), 1.71 (m, 1H), 1.61 (m, 1H), 1.30-1.52 (m, 2H), 0.86 (m, 6H). LC/MS $R_T$ 2.479 min.

Intermediate 7a

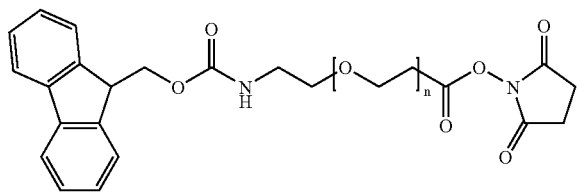

Boc-PEG-NHS MW 3400 Da (100 mg, 29.4 μmol) purchased from Nektar was stirred in 50% TFA in DCM containing 2% triisopropylsilane for 40 min, then the solution was evaporated to dryness, co-evaporated thrice with DCM and left on the vacuum line for 2 h. Nnmr of the crude (CDCl₃) clearly showed the removal of the Boc-group. Dissolved in acetonitrile-water, 1:1 (2 mL) and treated with Fmoc-OSu (12 mg, 35.61 μmol) and DIPEA (50 μL, 0.29 mmol) for 1 h. LC/MS (following the ionisation mode) showed fall conversion to a new product at $R_T$ 2.186 min, compared with the starting material $R_T$ 2.186 min (ionisation mode). The reaction mixture was concentrated to remove organics then diluted with water and freeze dried. The solid was triturated several times with ether, filtered and washed repeatedly with ether to give 104 mg. This was immediately dissolved in DCM (2.5 mL) and N-hydroxysuccinimide (4 mg, 34.78 μmol), DCC (7 mg, 34 μmol) and DIPEA (15 μL, 86.3 μmol) were sequentially added and the reaction mixture was stirred for 3.5 h. Filtered through a small plug of Celite, rotary evaporated to dryness and the solid was crystallised from ether, filtered, washed repeatedly with ether and dried in vacuum to give 105 mg (92% overall). Nmr (CDCl₃) of the crystalline material was difficult to accurately interpret.

Intermediate 7b

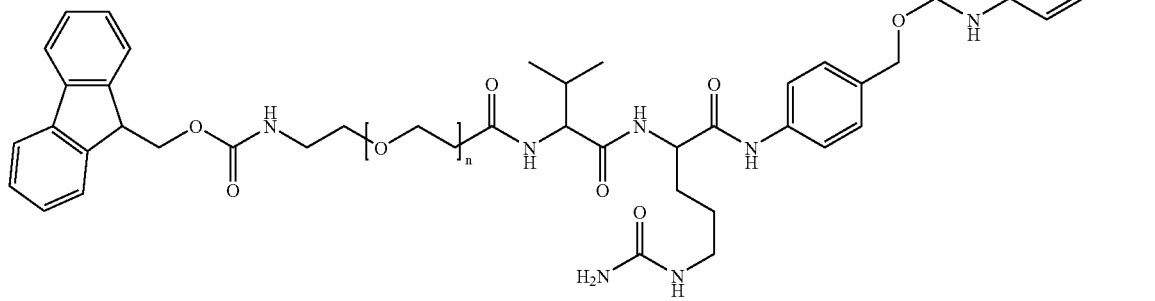

A mixture of 7a (100 mg, 28.393 μmol), 6b (16.5 mg, 28.4 μmol) and DIPEA (15 μL, 86.28 μmol) in DMF (1 mL) was stirred until LC/MS indicated the consumption of II (48 h). It was then evaporated to dryness and digester in ether-DCM, 4:1, filtered and washed with the same solvent then ether and dried to give 96 mg (85%). ¹H.n.m.r. (DMSO-d₆), δ 10.25 (s, 1H), 10.22 (s, 1H), 9.44 (s, 1H), 8.65 (m, 1H), 8.12 (m, 1H), 7.62-7.72 (m, 5H), 7.39-7.49 (m, 3H), 7.18 (m, 1H), 6.25 (s, 1H), 6.00 (m, 1H), 5.14 (s, 1H), 4.04 (m, 2H), 3.22-3.64 (m, includes PEG), 2.42 (m, 3H), 2.08 (m, 1H), 1.73 (m, 1H), 1.63 (m, 1H), 1.36-1.57 (m, 2H), 1.24 (m, 3H), 0.93 (m, 3H). $R_T$ for the ionisation peak 2.648 min.

Effector Species (VII)

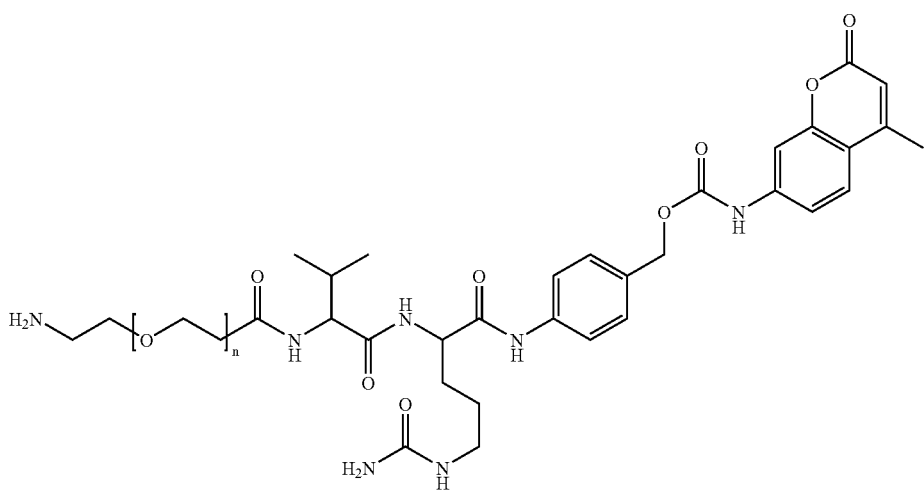

7b (86 mg, 21.56 μmol) in DMF (2 mL) was treated with 20% piperidine in DMF solution (1 mL) for 2 h. The resulting solution was rotary evaporated to dryness and the residual solid was digested in ether-DCM, 4:1, filtered, washed with the same solvent and dried (32 mg, 39%). $^1$H.n.m.r. (DMSO-$d_6$), δ 10.25 (s, 1H), 10.66 (s, 1H), 9.5 (b, 1H), 8.22 (b, 1H), 7.62-7.74 (m, 4H), 7.34-7.44 (m, 2H), 7.18 (m, 1H), 6.22 (s, 1H), 6.00 (m, 1H), 5.4 (s, 1H), 5.12 (b, 1H), 4.04 (m, 2H), 3.65 (m, 1H), 3.42-3.64 (m, includes PEG), 3.12 (m, 1H), 3.00 (m, 1H), 2.42 (m, 3H), 1.90 (m, 1H), 1.1.54-1.79 (m, 3H), 1.33-1.53 (m, 2H), 0.74-0.93 (m, 6H). $R_T$ for the ionisation peak 2.579 min.

Solubilising Species (i) 3-amino-1,2-propanediol
(ii) amino-dPEG™$_4$ alcohol purchased from Quanta Biodesign
(iii) m-dPEG™$_{12}$ amine purchased from Quanta Biodesign
(iv) m-dPEG™$_4$ amine purchased from Quanta Biodesign
(v) m-dPEG™$_{24}$ amine purchased from Quanta Biodesign
(vi) Ethanaminium, 2-[[(2-aminoethoxy)hydroxyphosphinyl]oxy]-N,N,N-trimethyl-, inner salt prepared as described in the literature A General Procedure for Polymer Loading The desired polymer (one of A-F) (usually 10-25 mg) is dissolved in anhydrous DMF (2-2.5 mL) by warming and the clear solution is then cooled to ambient temperature. The desired molar equivalents of the effector species (one of (I)-(VII)) to be loaded is added followed by twice this number of equivalents of DIPEA and the mixture stirred at 45° C. The progress of the reaction is followed by LC/S by monitoring the consumption of the effector species in the reaction mixture. On completion of the reaction (usually 24-48 h) an excess of the solubilising species (one of (i)-(vi)) is added and the reaction is stirred for a further 16-24 h, again at 45° C. All volatiles are then removed by rotary evaporation under reduced pressure and the residue dissolved in water and filtered through either Celite or a 0.2 μmeter filter. The filtrate is then transferred to a centrifugal filtration tube with a 5000 or 10000 NMCO membrane (depends on the molecular weight of the loaded polymer) and centrifugal filtration is carried out at 4000 rpm. The tube is replenished with fresh water and the process repeated for 4 times. All material unable to pass through the filter is collected and freeze dried to give the desired loaded polymer.

Loaded Polymer Example 1

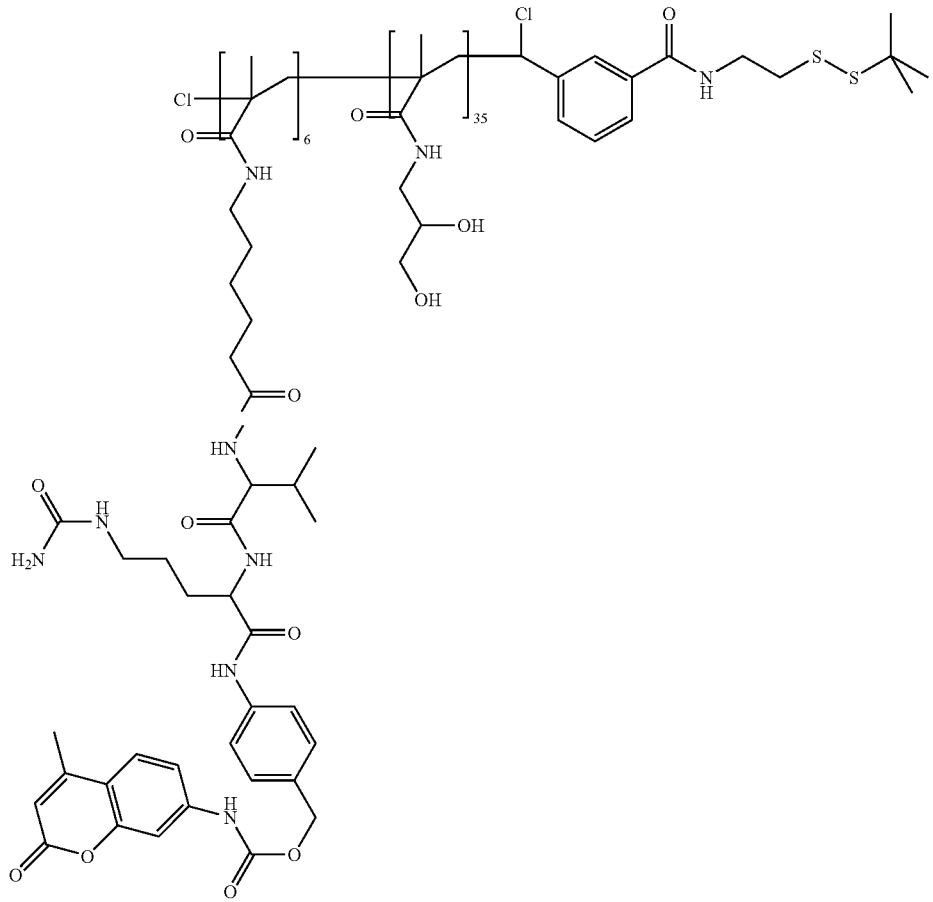

Based on Polymer C (DP = 41)

¹H.n.m.r. (DMSO-d₆), δ 10.00 (s), 7.10-8.15 (m), 6.23 (m), 5.36-5.4 (m), 5.05-5.12 (m), 4.25-4.45 (m), 4.08-4.24 (m), 2.78-3.71 (m, 2.64-2.76 (m), 0.5-2.4 (m).

It will be appreciated that the effector and solubilising moieties are attached randomly to the comb polymer backbone.

A General Procedure for the Disulfide Reduction of the Loaded Polymers.

The loaded polymer (usually 5-20 mg) is dissolved in phosphate buffer pH 7.8-8.0 (0.5-1 mL) and stirred under nitrogen. A solution of the reducing agent, tri-hydroxypropylphosphine (usually 5 molar equivalent) in the same buffer is then added and the reaction mixture stirred at room temperature for 4 h. After such time, the reaction mixture is diluted with carbonated water (~pH 5) and filtered through Celite or a 0.2 μmeter filter. The solution is then subjected to centrifugal filtration as described above using carbonated water, and freeze dried to give the thiol terminated loaded polymer in 80-95% yield.

Reduced Polymer Example 1

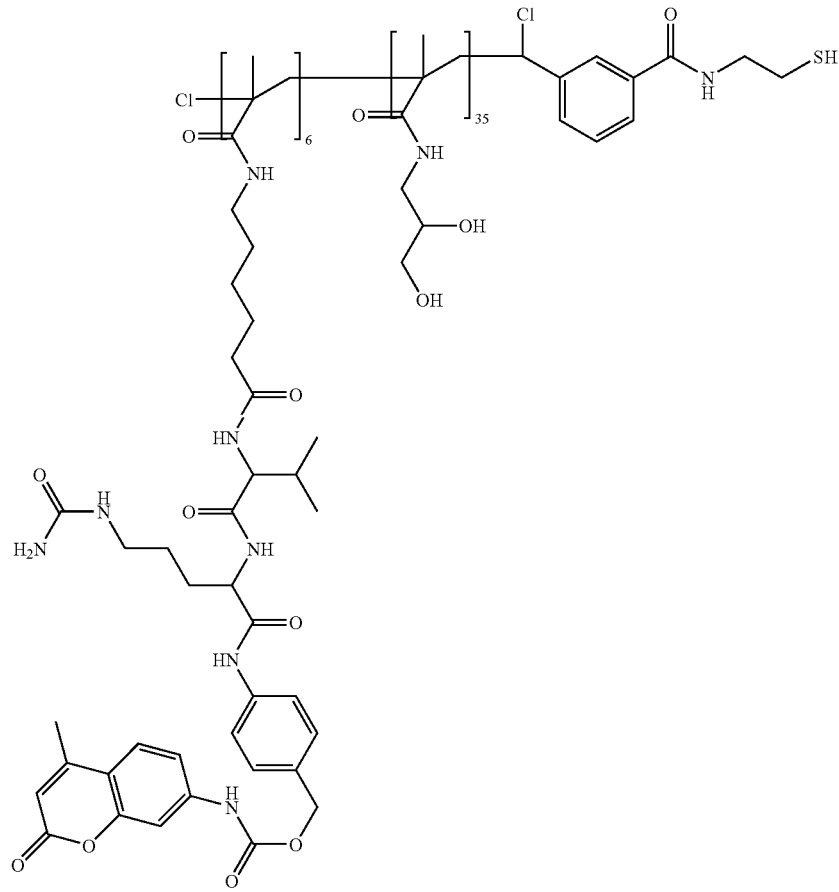

Based on Polymer C (DP = 41)

It will be appreciated that the effector and solubilising moieties are attached randomly to the comb polymer backbone.

A General Procedure for Maleimide Derivatisation of the Loaded Polymers.

To a solution of reduced polymer (approx 5 mg) in ethanol water, 1:1 (200 μL) is added a solution of 10 molar equivalents of a bis maleimide such as 1,11-bis-maleimidotetraethylene glycol also in ethanol-water, 1:1 (200 μL). After stirring for 1.5 h the reaction is diluted with water and subjected to centrifugal filtration as previously described.

Malemide Polymer Example 1

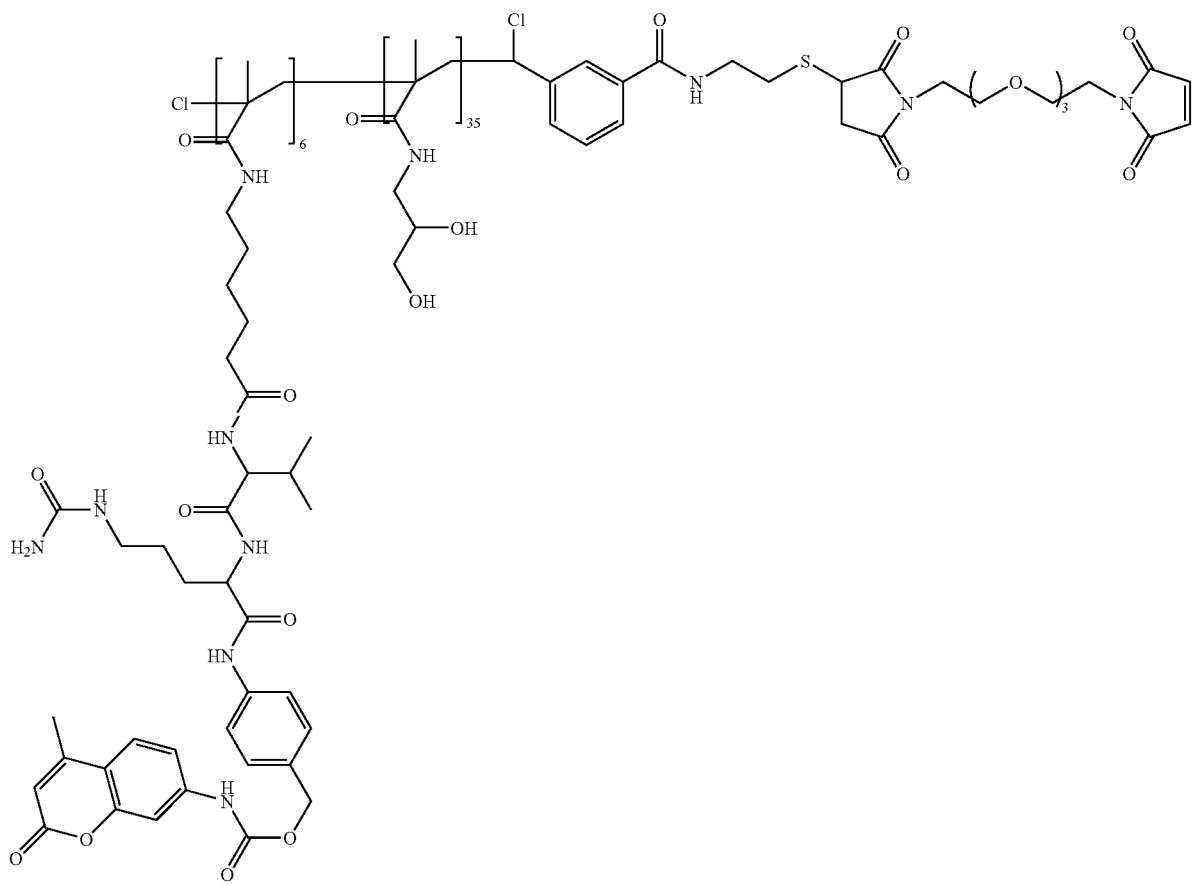

Based on Polymer C (DP = 41)

$^1$H.n.m.r. (DMSO-d$_6$), δ10.25 (s, 1H), 10.02 (s, 1H), 7.02-8.10 (m), 5.98-6.24 (m), 5.42-5.68 (m), 5.13 (bs), 4.30-5.05 (m), 2.60-3.94 (m), 2.36 (bs), 0.29-2.24 (m).

It will be appreciated that the effector and solubilising moieties are attached randomly to the comb polymer backbone.

Examples of Loaded Polymers Prepared

| Polymer | Effector Species/ number | Solublising Species | Loaded Polymer Yield | Polymer Reduced? | Polymer derivatised with maleimide? |
|---|---|---|---|---|---|
| C | (I)/6 | (i) | 110 mg (83%) | ✓ | ✓ |
| E | (I)/25 | (i) | 24 mg (71%) | ✓ | ✓ |
| E | (I)/50 | (i) | 15 mg (66%) | ✓ |  |
| C | (I)/12 | (i) | 11.5 mg (52%) | ✓ | ✓ |
| C | (II)/(6) | (i) | 18 mg (88%) | ✓ | ✓ |
| C | (II)/(12) | (i) | 25 mg (70%) |  |  |
| C | (I)/6 | (vi) | 30 mg (54%) |  |  |
| B | (III)/(2) | (i) | 22 mg (53%) |  |  |
| C | (I)/6 | (iv) | 12.1 mg (55%) |  |  |
| C | (III)/(6) | (ii) | 8.4 mg (70%) |  |  |
| C | (III)/(6) | (iii) | 18.1 mg (89%) |  | ✓ |
| B | (III)/(6) | (iii) | 13 mg (97%) |  | ✓ |
| B | (VII)/(13) | — | 16.9 mg (94%) |  | ✓ |
| C | (VI)/(6) | (v) | 12.1 mg (79%) |  | ✓ |

Examples of Loaded Polymers Prepared

| Polymer | Effector Species/number | Solublising Species | Loaded Polymer Yield | Polymer Reduced? | Polymer derivatised with maleimide? |
|---|---|---|---|---|---|
| C | (V)/(6) | (v) | 15 mg (88%) | | ✓ |
| C | (IV)/(6) | (iii) | 13.8 mg (66%) | | ✓ |

Polymer Conjugate 1

Method 1

Maleimide Polymer Example 1 in DMF was incubated with reduced Fab' (prepared by reduction with 5 mM 2-mercaptoethylamine for 30 min at 37° C. and removal of excess reductant by PD-10 column) in 0.1M sodium phosphate, 2 mM EDTA, pH 6.0 buffer. Maleimide Polymer Example 1:Fab' molar ratios of 2, 5, 10, 15, 20 and 25:1 were used. The final Fab' concentrations were 2 mg/ml and DMF was present at 20% final. The reaction mix was maintained at RT for 1 hr and overnight at 4° C. and then the extent of reaction determined by SDS PAGE analysis under both non-reducing and reducing conditions and by GPC HPLC in 0.2M phosphate, pH 7.0/10% EtOH.

Method 2

Reduced Fab' (prepared as above) was incubated with a 5 fold excess of 1,11-bismaleimidotetraethyleneglycol at RT for 1 hr and overnight at 4° C. Excess 1,11-bismaleimidotetraethyleneglycol was removed by PD-10 column and the resultant Fab'-(1,11-bismaleimidotetraethyleneglycol) conjugate was incubated with Reduced Polymer Example 1 in 0.1M sodium phosphate, 2 mM EDTA, pH 6.0 buffer at Intermediate 6:Fab' conjugate molar ratios 2, 5, 10, 15, 20 and 25:1. The final Fab' conjugate concentration were 2 mg/ml and DMF was present at 20% final.

Purification of Polymer Conjugate 1

Pooled reaction mixes from either of the above two methods were applied to a SP-Sepharose HP column in 50 mM sodium acetate, pH 4.50 buffer. Products were eluted using a salt gradient of 0-250 mM over 20 column volumes. The product was isolated as evidenced by analysis of fractions by SDS PAGE and by MALDI-TOF which showed that a species had been prepared and isolated with the correct molecular ion.

The invention claimed is:

1. The antibody-comb polymer conjugate produced by a process for producing a comb polymer comprising:
    a) providing:
        (i) (w+z) molar equivalents of a monomer, said monomer comprising an olefin unsaturation and an ester or amide linkage site;
        (ii) one molar equivalent of an initiator compound of formula (IX)

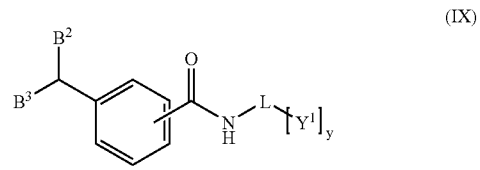

(IX)

wherein $B^3$ is a halogen, $B^2$ represents H or a halogen, $Y^1$ is a group capable of attaching the residue of an antibody or fragment thereof or capable of being converted into such a group, L is a linker group, y is 1, 2 or 3, w is at least 1, and z is 0 or greater;
        (iii) a catalyst capable of catalyzing the polymerization of the monomer to produce the comb polymer; and
    b) causing the catalyst to catalyze, in combination with the initiator, the polymerization of the monomer (i) to produce the comb polymer having a polymer backbone, said polymer backbone being bound to a molecule of said initiator at $B^3$;
    c) attaching at least one antibody or fragment thereof to at least one $Y^1$; and
    d) reacting the comb polymer produced in step b) with w equivalents of one or more effector molecules and z equivalents of one or more water solubilising moieties, wherein w is at least 1 and z is 0 or greater, and wherein said effector molecules are selected from one or more of the groups consisting of nucleic acids, carbohydrates, lipids, proteins, polypeptides, peptides, peptidomimetics, small molecules, cytotoxins, cytotoxic agents, antimetabolites, chelated radionuclides, enzymes, fluorescent materials, luminescent materials, bioluminescent materials, radioactive nuclides, positron emitting metals, nonradioactive paramagnetic metal ions, streptavidin, avidin, biotin, and straight or branched chain polyalkylene, polyalkenylene, or polyoxyalkylene polymers,
wherein step d) can occur either before or after step c), and wherein $Y^1$ does not react with said monomer ester or amide linkage site.

2. An antibody-comb polymer conjugate having the formula (Ia) or (Ib):

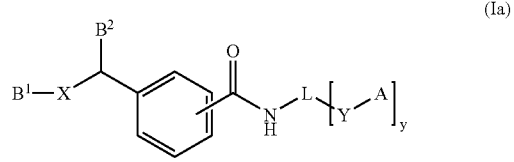

(Ia)

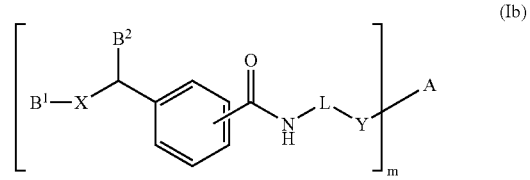

(Ib)

wherein:
B¹ is a halogen;
B² is H or a halogen;
L is a linker group
y is 1, 2 or 3;
m is 1, 2, 3, 4, 5, 6, 7, 8, 9 or 10;
A is an antibody or fragment thereof;
Y is a spacer group; and
X is a comb polymer moiety comprising a plurality of linkage sites, to which at least some of said linkage sites are attached w equivalents of one or more effector molecules with an optional linker group between said linkage site and said effector molecule, and z equivalents of one or more water solubilising moieties, wherein w is at least 1 and z is 0 or greater, and wherein said effector molecules are selected from one or more of the groups consisting of nucleic acids, carbohydrates, lipids, proteins, polypeptides, peptides, peptidomimetics, small molecules, cytotoxins, cytotoxic agents, antimetabolites, chelated radionuclides, enzymes, fluorescent materials, luminescent materials, bioluminescent materials, radioactive nuclides, positron emitting metals, nonradioactive paramagnetic metal ions, streptavidin, avidin, biotin, and straight or branched chain polyalkylene, polyalkenylene, or polyoxyalkylene polymers; and wherein Y is not reactive with said monomer linkage sites.

3. The antibody-comb polymer conjugate according to claim 2, wherein X comprises the components of formula III and IV in any order

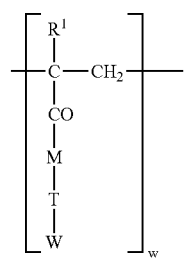

(III)

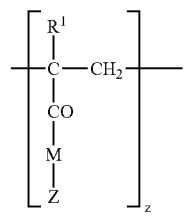

(IV)

wherein:
w is at least 1 and z is 0 or greater;
T is absent or a linker group
W is an effector molecule;
Z is a water solubilising moiety;
M is NH or O; and
R¹ is methyl or H.

4. A pharmaceutical composition comprising an antibody-comb polymer conjugate according to claim 2 in association with one or more pharmaceutically acceptable carriers, excipients or diluents.

5. The antibody-comb polymer conjugate according to claim 2, wherein B² is H.

6. The antibody-comb polymer conjugate according to claim 2, wherein L is: —$(CH_2)_n$— wherein n is 1, 2, 3, 4, 5 or 6; or

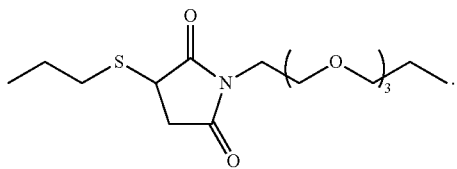

7. The antibody-comb polymer conjugate according to claim 2, wherein Y is succinimide.

8. The antibody-comb polymer conjugate according to claim 3, wherein T is a linker of formula (V):

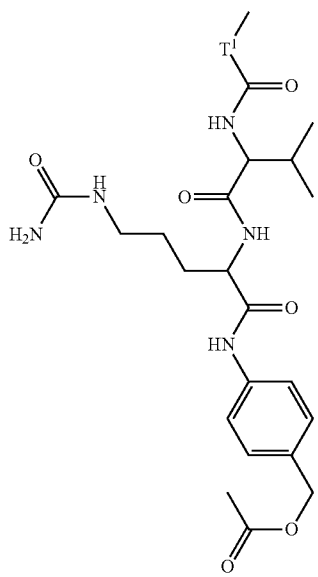

(V)

wherein $T^1$ represents $[CH_2]_t$ or $CH_2CH_2[OCH_2CH_2]_n$ where t is between 1 and 10 and n is between 5 and 100.

9. The antibody-comb polymer conjugate according to claim 3, wherein Z is selected from:

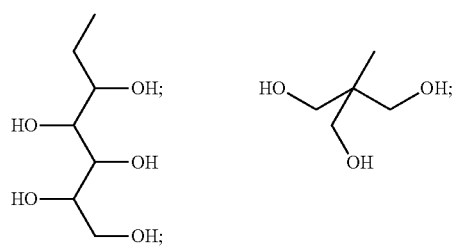

10. An antibody-comb polymer conjugate according to claim 2:
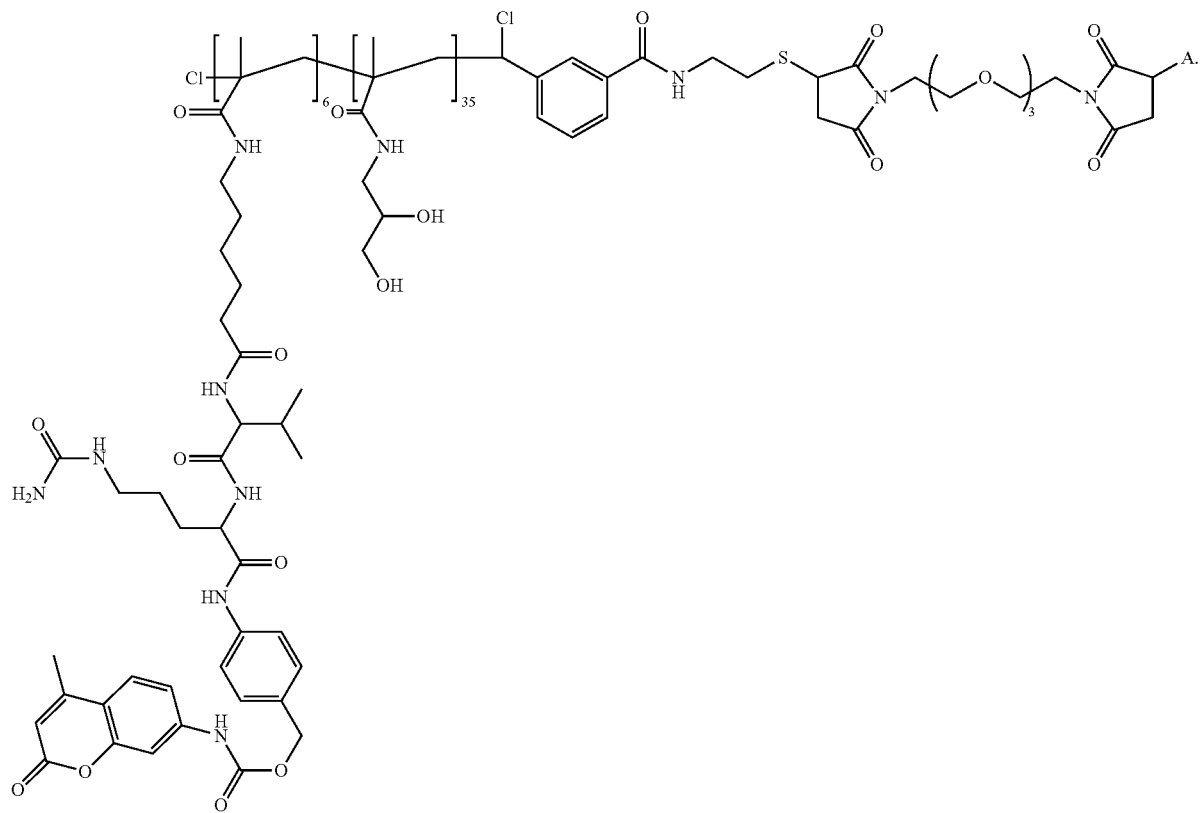
* * * * *